United States Patent
Pinter et al.

(10) Patent No.: US 9,224,181 B2
(45) Date of Patent: Dec. 29, 2015

(54) SYSTEMS AND METHODS FOR VISUALIZING PATIENT AND TELEPRESENCE DEVICE STATISTICS IN A HEALTHCARE NETWORK

(71) Applicant: INTOUCH TECHNOLOGIES, INC., Goleta, CA (US)

(72) Inventors: Marco Pinter, Goleta, CA (US); Greg Brallier, Goleta, CA (US); Scott Ross, Santa Barbara, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days.

(21) Appl. No.: 14/528,207

(22) Filed: Oct. 30, 2014

(65) Prior Publication Data
US 2015/0057927 A1    Feb. 26, 2015

Related U.S. Application Data

(63) Continuation of application No. 13/558,059, filed on Jul. 25, 2012, now Pat. No. 8,902,278, which is a continuation-in-part of application No. 13/444,106, filed on Apr. 11, 2012.

(51) Int. Cl.
*H04M 7/14*    (2006.01)
*G06Q 50/22*    (2012.01)
(Continued)

(52) U.S. Cl.
CPC .............. *G06Q 50/22* (2013.01); *G06F 3/0484* (2013.01); *G06F 19/327* (2013.01); *G06F 19/3418* (2013.01); *G06Q 10/101* (2013.01)

(58) Field of Classification Search
CPC ........................................................ H04N 7/14
USPC ........... 348/14.01, 14.05, 14.03, 14.04, 14.07
See application file for complete search history.

(56) References Cited

U.S. PATENT DOCUMENTS

| 4,107,689 A | 8/1978 | Jellinek |
| 4,213,182 A | 7/1980 | Eichelberger et al. |

(Continued)

FOREIGN PATENT DOCUMENTS

| CN | 1404695 A | 3/2003 |
| CN | 1561923 A | 1/2005 |

(Continued)

OTHER PUBLICATIONS

"Nomad Scout User's Manual", Nomadic Technologies, Software Version 2. 7, Part No. DOC00004, Jul. 12, 1999, pp. 1-59.

(Continued)

*Primary Examiner* — Olisa Anwah

(57) ABSTRACT

Disclosed herein are various embodiments of systems and methods for visualizing, analyzing, and managing telepresence devices operating in a telepresence network of healthcare facilities. A user may selectively view a global view of all telepresence devices, telepresence devices within a particular region, the details of a particular telepresence device, and/or the details of a particular healthcare facility. At one viewing level, a user may view a plan view map of a healthcare facility and visualize the navigational history of a telepresence device. At another viewing level, a user may view a plan view map of a healthcare facility and visualize telemetry data of a patient associated with a selected room. At another viewing level, a user may selectively view various graphical representations of telepresence device statistics and usage information with respect to health ratings for each of a plurality of patients.

11 Claims, 21 Drawing Sheets

(51) Int. Cl.
*G06F 3/0484* (2013.01)
*G06Q 10/10* (2012.01)
*G06F 19/00* (2011.01)

(56) References Cited

U.S. PATENT DOCUMENTS

| | | | |
|---|---|---|---|
| 4,553,309 | A | 11/1985 | Hess et al. |
| 4,697,278 | A | 9/1987 | Fleischer |
| 5,617,539 | A | 4/1997 | Ludwig et al. |
| 5,867,494 | A | 2/1999 | Krishnaswamy et al. |
| 6,091,219 | A | 7/2000 | Maruo et al. |
| 6,292,714 | B1 | 9/2001 | Okabayashi |
| 6,314,631 | B1 | 11/2001 | Pryor |
| 6,317,953 | B1 | 11/2001 | Pryor |
| 6,373,855 | B1 | 4/2002 | Downing et al. |
| 6,411,055 | B1 | 6/2002 | Fujita et al. |
| 6,567,038 | B1 | 5/2003 | Granot et al. |
| 6,667,592 | B2 | 12/2003 | Jacobs et al. |
| 6,674,259 | B1 | 1/2004 | Norman et al. |
| 6,693,585 | B1 | 2/2004 | MacLeod |
| 6,816,754 | B2 | 11/2004 | Mukai et al. |
| 6,893,267 | B1 | 5/2005 | Yueh |
| 6,990,112 | B1 | 1/2006 | Brent et al. |
| 7,011,538 | B2 | 3/2006 | Chang |
| 7,053,578 | B2 | 5/2006 | Diehl et al. |
| 7,055,210 | B2 | 6/2006 | Keppler et al. |
| 7,222,000 | B2 | 5/2007 | Wang et al. |
| 7,292,257 | B2 | 11/2007 | Kang et al. |
| 7,332,890 | B2 | 2/2008 | Cohen et al. |
| 7,333,642 | B2 | 2/2008 | Green |
| 7,352,153 | B2 | 4/2008 | Yan |
| 7,363,121 | B1 | 4/2008 | Chen et al. |
| 7,467,211 | B1 | 12/2008 | Herman et al. |
| 7,483,867 | B2 | 1/2009 | Ansari et al. |
| 7,510,428 | B2 | 3/2009 | Obata et al. |
| 7,557,758 | B2 | 7/2009 | Rofougaran |
| 7,631,833 | B1 | 12/2009 | Ghaleb et al. |
| 7,657,560 | B1 | 2/2010 | DiRienzo |
| 7,703,113 | B2 | 4/2010 | Dawson |
| 7,737,993 | B2 | 6/2010 | Kaasila et al. |
| 7,861,366 | B2 | 1/2011 | Hahm et al. |
| 8,126,960 | B2 | 2/2012 | Obradovich et al. |
| 8,212,533 | B2 | 7/2012 | Ota |
| 8,320,534 | B2 | 11/2012 | Kim et al. |
| 8,374,171 | B2 | 2/2013 | Cho et al. |
| 8,400,491 | B1 | 3/2013 | Panpaliya et al. |
| 8,401,275 | B2 | 3/2013 | Wang et al. |
| 8,423,284 | B2 | 4/2013 | O'Shea |
| 8,451,731 | B1 | 5/2013 | Lee et al. |
| 8,489,641 | B1 | 7/2013 | Seefeld et al. |
| 8,515,577 | B2 | 8/2013 | Wang et al. |
| 8,610,786 | B2 | 12/2013 | Ortiz |
| 8,612,051 | B2 | 12/2013 | Norman et al. |
| 8,639,797 | B1 | 1/2014 | Pan et al. |
| 8,670,017 | B2 | 3/2014 | Stuart et al. |
| 8,726,454 | B2 | 5/2014 | Gilbert et al. |
| 8,750,906 | B2 | 6/2014 | Winkler et al. |
| 8,776,043 | B1 | 7/2014 | Thimsen et al. |
| 8,836,751 | B2 | 9/2014 | Ballantyne et al. |
| 8,849,679 | B2 | 9/2014 | Wang et al. |
| 8,849,680 | B2 | 9/2014 | Wright et al. |
| 8,861,750 | B2 | 10/2014 | Roe et al. |
| 8,897,920 | B2 | 11/2014 | Wang et al. |
| 8,902,278 | B2 | 12/2014 | Pinter et al. |
| 2002/0109775 | A1 | 8/2002 | White et al. |
| 2002/0123941 | A1 | 9/2002 | Donahue et al. |
| 2002/0128985 | A1 | 9/2002 | Greenwald |
| 2003/0112823 | A1 | 6/2003 | Collins et al. |
| 2003/0135097 | A1 | 7/2003 | Wiederhold et al. |
| 2003/0195662 | A1 | 10/2003 | Wang et al. |
| 2003/0216833 | A1 | 11/2003 | Mukai et al. |
| 2004/0008138 | A1 | 1/2004 | Hockley, Jr. et al. |
| 2004/0218099 | A1 | 11/2004 | Washington |
| 2004/0243712 | A1 | 12/2004 | Sakai et al. |
| 2004/0260790 | A1 | 12/2004 | Balloni et al. |
| 2005/0073575 | A1 | 4/2005 | Thacher et al. |
| 2005/0125083 | A1 | 6/2005 | Kiko |
| 2005/0149364 | A1 | 7/2005 | Ombrellaro |
| 2005/0264649 | A1 | 12/2005 | Chang et al. |
| 2005/0286759 | A1 | 12/2005 | Zitnick et al. |
| 2006/0056655 | A1 | 3/2006 | Wen et al. |
| 2006/0056837 | A1 | 3/2006 | Vapaakoski |
| 2006/0066609 | A1 | 3/2006 | Iodice et al. |
| 2006/0071797 | A1 | 4/2006 | Rosenfeld et al. |
| 2006/0238379 | A1 | 10/2006 | Kimchi et al. |
| 2007/0093279 | A1 | 4/2007 | Janik |
| 2007/0116152 | A1 | 5/2007 | Thesling |
| 2007/0170886 | A1 | 7/2007 | Plishner |
| 2007/0226949 | A1 | 10/2007 | Hahm et al. |
| 2007/0290040 | A1 | 12/2007 | Wurman et al. |
| 2008/0051985 | A1 | 2/2008 | D'Andrea et al. |
| 2008/0091340 | A1 | 4/2008 | Milstein et al. |
| 2008/0161969 | A1 | 7/2008 | Lee et al. |
| 2008/0232763 | A1 | 9/2008 | Brady |
| 2008/0263628 | A1 | 10/2008 | Norman et al. |
| 2008/0267069 | A1 | 10/2008 | Thielman et al. |
| 2009/0049640 | A1 | 2/2009 | Lee et al. |
| 2009/0102919 | A1 | 4/2009 | Zamierowski et al. |
| 2009/0259339 | A1* | 10/2009 | Wright et al. ............ 700/264 |
| 2010/0026239 | A1 | 2/2010 | Li et al. |
| 2010/0066804 | A1 | 3/2010 | Shoemake et al. |
| 2010/0171826 | A1 | 7/2010 | Hamilton et al. |
| 2010/0278086 | A1 | 11/2010 | Pochiraju et al. |
| 2010/0301679 | A1 | 12/2010 | Murray et al. |
| 2011/0022705 | A1 | 1/2011 | Yellamraju et al. |
| 2011/0071675 | A1 | 3/2011 | Wells et al. |
| 2011/0072114 | A1 | 3/2011 | Hoffert et al. |
| 2011/0193949 | A1 | 8/2011 | Nambakam et al. |
| 2011/0280551 | A1 | 11/2011 | Sammon |
| 2012/0059946 | A1 | 3/2012 | Wang |
| 2012/0113856 | A1 | 5/2012 | Krishnaswamy |
| 2012/0203731 | A1 | 8/2012 | Nelson et al. |
| 2012/0291809 | A1 | 11/2012 | Kuhe et al. |
| 2013/0250938 | A1 | 9/2013 | Anandakumar et al. |
| 2013/0321257 | A1 | 12/2013 | Moore et al. |
| 2014/0032244 | A1 | 1/2014 | Kolls et al. |
| 2014/0047022 | A1 | 2/2014 | Chan et al. |
| 2014/0085543 | A1 | 3/2014 | Hartley et al. |
| 2014/0135990 | A1 | 5/2014 | Stuart et al. |
| 2014/0139616 | A1 | 5/2014 | Pinter et al. |
| 2014/0155755 | A1 | 6/2014 | Pinter et al. |
| 2014/0250191 | A1 | 9/2014 | Altman et al. |
| 2015/0053689 | A1 | 2/2015 | Chhina |

FOREIGN PATENT DOCUMENTS

| | | |
|---|---|---|
| CN | 1743144 A | 3/2006 |
| CN | 101049017 A | 10/2007 |
| CN | 101151614 A | 3/2008 |
| CN | 100407729 C | 7/2008 |

OTHER PUBLICATIONS

ACM Digital Library Record, "Autonomous Robots vol. 11 Issue 1", downloaded from <http://dl.acm.org/citation.cfm?id=591550&picked=prox&cfid=360891374&cftoken=35225929>, Jul. 2001, 2 pages.

Brenner, "A technical tutorial on the IEEE 802.11 protocol", BreezeCOM Wireless Communications, 1997, pp. 1-24.

Library of Congress, "008- Fixed-Length Data Elements (NR)", MARC 21 Format for Classification Data, downloaded from http://www.loc.gov/marc/classification/cd008.html, Jan. 2000, pp. 1-14.

Paulos, et al., "Personal Tele-Embodiment", Chapter 9 in Goldberg, et al., ed. "Beyond webcams", MIT Press, Jan. 4, 2002, pp. 155-167.

Paulos, "Personal tele-embodiment", OskiCat Catalog Record, UCB Library Catalog, 2001, 3 pages.

Paulos, "Personal Tele-Embodiment", Introductory and cover pages from 2001 Dissertation including Contents table, together with e-mails relating thereto from UC Berkeley Libraries, as shelved at UC Berkeley Engineering Library (Northern Regional library Facility), May 8, 2002, 25 pages, including 4 pages of e-mails.

(56) References Cited

OTHER PUBLICATIONS

Paulos, et al., "Social Tele-Embodiment: Understanding Presence", Autonomous Robots, vol. 11, Issue 1, Kluwer Academic Publishers, Jul. 2001, pp. 87-95.

Screenshot Showing Google Date for Lemaire Telehealth Manual, Screenshot Retrieved on Dec. 18, 2014, 1 page.

Nomadic Technologies, Inc., "Nomad Scout Language Reference Manual", Software Version: 2.7, Part No. DOC00002, Jul. 12, 1999, 47 pages.

Fulbright et al., "Swami: An Autonomous Mobile Robot for Inspection of Nuclear Waste of Storage Facilities", Autonomous Robots, vol. 2, 1995, pp. 225-235.

* cited by examiner

FIG. 14

| Patient ID | OUTCOME | Prim.Phys | Condition | Room | #visits/day | Stethoscope | Zoom>50% | Patient | Staff | Monitor | Chart | Other | In Room | Bedside | Driving |
|---|---|---|---|---|---|---|---|---|---|---|---|---|---|---|---|
| | | | | | | | Looking at | | | | | | Location | | |
| | | | | | | | | | | TIME SPENT | | | | | |
| 127 | 0.0 | Smith | Cardio | 1004 | 1 | 4 | 5 | 8 | 2 | 3 | 0 | 2 | 15 | 5 | 8 |
| 103 | 0.0 | Johnson | Cardio | 1001 | .33 | 0 | 0 | 3 | 2 | 0 | 0 | 0 | 5 | 1 | 5 |
| 120 | 12.5 | Johnson | Resp. | 1002 | 0.5 | 0 | 5 | 5 | 2 | 0 | 2 | 3 | 12 | 10 | 8 |
| 127 | 25.7 | Johnson | Cardio | 1005 | 0.66 | 1 | 9 | 9 | 1 | 3 | 0 | 2 | 15 | 2 | 12 |
| 109 | 34.8 | Smith | Neuro | 1001 | 1 | 2 | 2 | 3 | 5 | 4 | 0 | 0 | 12 | 2 | 9 |
| 112 | 44.2 | Smith | Cardio | 1004 | 2 | 1 | 12 | 12 | 3 | 4 | 6 | 1 | 19 | 15 | 4 |
| 104 | 61.2 | Taylor | Resp. | 1002 | 1.66 | 1 | 1 | 1 | 6 | 8 | 3 | 9 | 22 | 15 | 8 |
| 125 | 65.5 | Smith | Resp. | 1005 | 1.5 | 2 | 0 | 6 | | 0 | 0 | 1 | 18 | 12 | 15 |
| 116 | 66.1 | Smith | Neuro | 1006 | 1.66 | 0 | 8 | 12 | 11 | 1 | 3 | 1 | 25 | 5 | 19 |
| 118 | 71.2 | Taylor | Neuro | 1004 | 2 | 1 | 10 | 18 | 5 | 7 | 0 | 3 | 33 | 30 | 9 |
| 114 | 78.8 | Johnson | Resp. | 1002 | 2.5 | 3 | 18 | 18 | 1 | 1 | 2 | 2 | 28 | 22 | 13 |
| 122 | 81.4 | Smith | Neuro | 1001 | 3 | 4 | 14 | 16 | 3 | 3 | 5 | 4 | 26 | 20 | 11 |
| 123 | 82.0 | Johnson | Cardio | 1005 | 3.5 | 1 | 4 | 9 | 20 | 5 | 2 | 9 | 38 | 18 | 5 |
| 115 | 88.9 | Johnson | Resp. | 1003 | 3 | 4 | 8 | 8 | 20 | 0 | 0 | 12 | 40 | 20 | 7 |
| 126 | 91.5 | Smith | Neuro | 1004 | 2.5 | 0 | 19 | 12 | 12 | 9 | 3 | 5 | 36 | 12 | 6 |
| 103 | 95.1 | Smith | Resp. | 1002 | 5 | 3 | 13 | 12 | 12 | 4 | 3 | 2 | 44 | 40 | 8 |
| 101 | 98.3 | Smith | Neuro | 1001 | 3.3 | 1 | 18 | 30 | 5 | | | | 45 | 5 | 5 |

SYSTEMS AND METHODS FOR VISUALIZING PATIENT AND TELEPRESENCE DEVICE STATISTICS IN A HEALTHCARE NETWORK

TECHNICAL FIELD

This disclosure relates to managing telepresence devices in healthcare networks. More specifically, this disclosure provides various visualization and management systems for use with telepresence devices, healthcare networks, and associated information.

BRIEF DESCRIPTION OF THE DRAWINGS

Non-limiting and non-exhaustive embodiments of the disclosure are described herein, including various embodiments of the disclosure illustrated in the figures listed below.

FIG. 14 illustrates a table of patients, outcome ratings, and telepresence device statistics associated with each of the patients.

Figure 1:
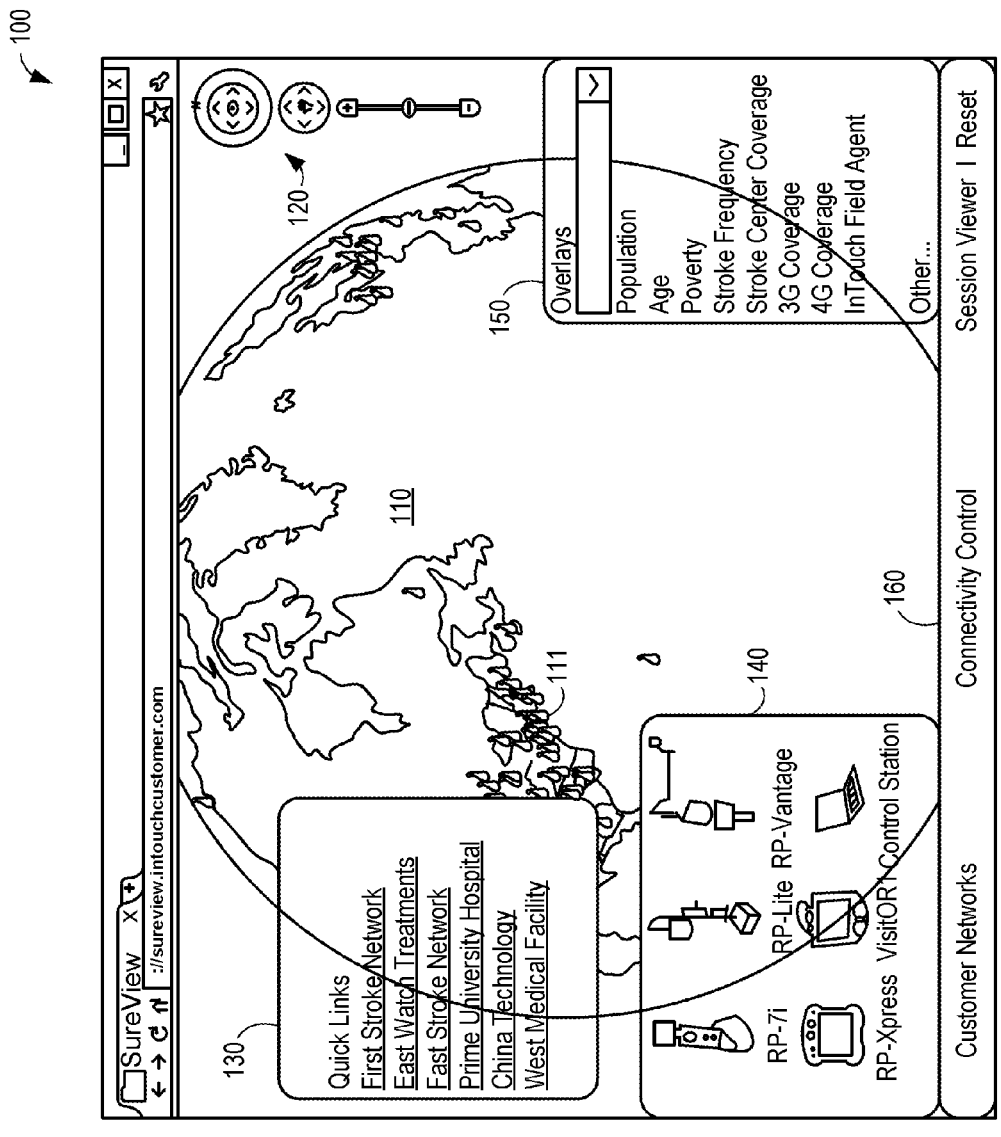
FIG. 1 illustrates a viewing level including a geographical representation of the world, shortcut links to various geographical locations, selectable icons associated with various device types, a navigation input panel, and selectable overlays.

The described features, structures, and/or characteristics of the systems and methods described herein may be combined in any suitable manner in one or more alternative embodiments, and may differ from the illustrated embodiments.

DETAILED DESCRIPTION

The present disclosure provides various systems and methods for visualizing and managing telepresence devices within healthcare networks and facilities. Using the presently described visualization and management tool, users may more efficiently visualize, analyze, and actively manage various aspects of a telepresence healthcare network. In some embodiments, a user may view a geographical representation of the relative location of each of a plurality of telepresence devices in a telepresence network.

Healthcare facilities may include telemedicine technologies, such as telepresence devices in a telepresence network, that allow remote healthcare practitioners to provide services to patients and/or other healthcare practitioners in remote locations. For example, a remote medical professional may be a neurologist practicing in a major hospital who may, via telepresence devices, provide services and consultations to patients and other medical professionals in hospitals located in rural areas that may otherwise not have a neurologist on staff.

The telepresence devices may operate as part of a telepresence network associated with one or more healthcare networks. Each healthcare network may include one or more healthcare facilities (e.g., hospitals, rehabilitation facilities, and long-term care facilities) that each have one or more telepresence devices. Types of telepresence devices include, but are not limited to, remote telepresence devices, mobile telepresence units, and/or control stations. For example, a remote telepresence device may include a telepresence robot configured to move within a medical facility and provide a means for a remote practitioner to perform remote consultations.

A visualization and management system for telepresence devices may be configured to display a first viewing level that includes a geographical representation of the location of various telepresence devices. The viewing level may include all telepresence devices, those within predefined geographical boundaries, those associated with a particular healthcare network, or those associated with a particular healthcare facility. The telepresence devices and/or healthcare facilities may also be displayed as hub devices/facilities and spoke devices/facilities. The various interconnections between the hubs and spokes may be selectively displayed.

A navigation control panel may allow a user to navigate within the geographical representation. For example, the navigation panel may allow for panning, tilting, scrolling, compass alignments, and/or other navigational options. Additionally, the field of view may be dynamically modified based on a user's selection. For example, the field of view may be controlled by a zooming panel or icon, or alternatively may be dynamically adjusted based on other navigational or icon selections. The information associated with the displayed telepresence devices and/or healthcare facilities may be limited or expanded based on the number of telepresence devices and/or healthcare facilities currently displayed in the selected field of view. In some embodiments, shortcuts may allow a user to quickly navigate to a specific geographical location, to a specific medical facility, to a specific medical network, and/or to a specific telepresence device.

The first viewing level may include various icons, panels, buttons, and/or other selectable options configured to allow a user to select one or more alternative viewing levels. For example, a device detail request module may allow a user to submit a detail request in order to view detailed information associated with one or more telepresence devices, healthcare facilities, and/or healthcare practitioners shown on the geographical representation. A user may request additional details by selecting a particular telepresence device and/or healthcare facility. In some embodiments, additional details may be presented when a user mouses over a device/facility. The mouse-over may cause a pop-up overlay to appear displaying additional details associated with the device/facility. The details associated with one or more telepresence devices may include the connection strength, the number of active sessions, a history of technical problems, a history of session activity, shipping information associated with a telepresence device, information associated with a software update, information associated with a firmware update, a serial number, a model number, a battery level, a date the telepresence device last reported, a time the telepresence device last reported, historical session data, a registered peripheral, a licensed application, a total utilization time, an average session duration, a duration of a particular session, a start time of a particular session, an end time of a particular session, a Quality of Service (QoS) for one or more sessions, a current available bandwidth, a bandwidth availability with respect to time, a current location of a telepresence device, and historical locations of a telepresence device with respect to time.

Similarly, the details associated with one or more healthcare facilities may include a number of active sessions, a number of active telepresence devices, a connection strength of telepresence devices, a connection between two or more telepresence devices, a location of a telepresence device, information from a StrokeRESPOND application, a door-to-needle time, a door-to-balloon time, t-PA contraindication and warning information, a healthcare practitioner response time, and a call center response time.

Additionally, details associated with a particular telepresence device, healthcare facility, healthcare network, and/or healthcare practitioner may include one or more connection rules. For example, connection rules may define where, when, and how a healthcare facility, healthcare network, and/or healthcare practitioner may access, view, monitor, and/or control a particular telepresence device or set of telepresence devices. The connection rules may also define who is granted access and what devices they can view. In some embodiments, a viewing level displaying one or more connection rules may allow a user to manage and/or configure the various connection rules between devices, facilities, and/or practitioners. In one embodiment, connection rules may be managed using drag-and-drop actions between devices, facilities, and/or practitioners.

Some of the viewing levels may include geographical representations constrained by particular geographical boundaries, the extent of a healthcare network, or the location of associated telepresence devices. Some of the viewing levels may include selectable overlays configured to overlay information on the geographical representations. Accordingly, a user may apply an informational overlay to a geographical representation that includes various healthcare facilities and/or telepresence devices.

Examples of overlays include, but are not limited to, a population density, a stroke frequency, an adoption rate of a software update, an adoption rate of a firmware update, a frequency of a particular medical condition, a frequency of a particular technical difficulty, an average age of the population, an average age of patients, socioeconomic conditions, an availability of wireless communications, a relative location of medical practitioners, active sessions, a data connection strength, and a relative location of support technicians. The informational overlay may be overlaid on the geographical representation as a heat map, as graphics, as pictures, as icons, as numbers, and/or as text.

In some embodiments, the informational overlay may be overlaid on the entire geographical representation. In other embodiments, the informational overlay may be overlaid on a portion of the geographical representation. For example, the informational overlay may only be overlaid on the portion of a geographical representation that corresponds to a geographical area serviced by a particular healthcare network, hospital, hub hospital, spoke hospital, telepresence device, support technician, and/or medical practitioner.

In some embodiments, a viewing level may include a geographical representation displaying the relative location of various telepresence devices. The viewing level may include various selectable device icons that each correspond to a particular type of telepresence device. The device icons may be used to toggle between displaying and not displaying the associated type of telepresence device. Accordingly, a user may toggle the device icons in order to view all of the control stations, but not the mobile telepresence units or the remote telepresence robots. Within the same viewing level, the user may toggle the device icons to view the remote telepresence robots and/or the mobile telepresence units, but not the control stations. Additional device icons may further differentiate between device types, models, vintages, active telepresence devices, inactive telepresence devices, and/or other characteristics of the various telepresence devices.

The visualization and management of telepresence networks may allow healthcare facilities, healthcare networks, healthcare practitioners, technical support personnel, and/or other users to improve patient care, provide enhanced telepresence services, reduce the costs associated with telepresence consultations, and/or otherwise improve existing technologies and systems. Suitable networks for use with the present visualization and management systems include any of a wide variety of physical infrastructures, protocols, connections, and encryption algorithms. According to various embodiments, networking practices may be implemented in order to comply with accepted healthcare standards and/or government regulations.

Some viewing levels may include plan map views allowing a user to visualize navigational paths of a telepresence device on one or more floors of a healthcare facility. In some embodiments, a user may visualize and distinguish between navigational paths in which a telepresence device was in an automated mode and navigational paths in which the telepresence device was in a teleoperated mode. Additionally, in one viewing level a user may select (e.g., via a click or a mouse-over) a room and view telemetry data associated with a patient in the selected room for a given time period.

Additionally, various viewing levels may allow a user to selectively visualize and filter data associated with patients, healthcare practitioners (e.g., a primary physician), and telepresence device statistics related to the usage of a telepresence device with respect to a particular patient or by a particular healthcare practitioner. In various examples, a coordinate system may be selectively populated with various graphs of telepresence device statistics, as described herein. The graphs may be filtered based on various criteria as selected by the user. The visualization may allow a user to easily and quickly find correlations between the manner in which a telepresence device is used and the outcome of a patient.

Various aspects of this disclosure are also described in U.S. patent application Ser. No. 13/444,106, filed Apr. 11, 2012 titled "SYSTEMS AND METHODS FOR VISUALIZING AND MANAGING TELEPRESENCE DEVICES IN HEALTHCARE NETWORKS," which application is incorporated herein by reference in its entirety.

The term "coordinate system" may refer to any type of organized visual or graphical representation of data. For example, a coordinate system may comprise, utilize, and/or incorporate a bar graph, a line chart, a plot, a diagram, a pie chart, a number line, a Cartesian coordinate system, a histogram, a cylindrical and/or spherical coordinate system, a timeline, a cartogram, a pedigree chart, a bubble chart, a polar area diagram, a waterfall chart, a tree, a polar coordinate system, a mapping, a radar chart, a distribution system, a scattergram, a Gantt chart, a Smith chart, a Nolan chart, a scatterplot, a color-coordinated data set, and/or other visual representation of data. The term "graph" as used herein may refer to any type of data representation within a coordinate system. For example, a graph may be a line drawn on a Cartesian coordinate system, a slice of a pie chart, a point on a scattergram, and/or other data representation on a coordinate system as defined herein.

Reference throughout this specification to "one embodiment" or "an embodiment" means that a particular feature, structure, or characteristic described in connection with the embodiment is included in at least one embodiment. Thus, the appearances of the phrases "in one embodiment" and "in an embodiment" in various places throughout this specification are not necessarily all referring to the same embodiment. In particular, an "embodiment" may be a system, an article of manufacture (such as a computer-readable storage medium), a method, and/or a product of a process.

The phrases "connected to" and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless otherwise specified.

Embodiments may include various features, which may be embodied in machine-executable instructions executed by a general-purpose or special-purpose computer (or other electronic device). Alternatively, the features may be performed by hardware components that include specific logic for performing the steps or by a combination of hardware, software, and/or firmware. Accordingly, the various components, modules, systems, and/or features described herein may be embodied as modules within a system. Such a system may be implemented in software, firmware, hardware, and/or physical infrastructure.

Embodiments may also be provided as a computer program product including a non-transitory machine-readable medium having stored thereon instructions that may be used to program or be executed on a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable media suitable for storing electronic instructions.

FIG. 1 illustrates a global viewing level 100 of a geographical representation of the world 110. As illustrated, the global viewing level 100 may include a navigation panel 120 with various icons configured to allow a user to pan, rotate, tilt, and zoom within the global viewing level. For instance, a slider bar may be slid between a "−" sign and a "+" sign in order to control the field of view of the geographical representation 110. A wide field of view may include the entire globe, as illustrated, and a narrow field of view may be limited to a single telepresence device and/or healthcare facility. The global viewing level 100 may include various quick links 130. A user may use the quick links 130 to navigate to a specific location on the geographical representation 110 and/or automatically adjust the field of view.

The viewing level 100 may also include a panel 140 of device-type icons. By selecting a device icon in the panel 140, a user may choose whether or not the particular device type is displayed on the geographical representation 110. For example, the illustrated viewing level 100 displays icons representing various telepresence devices on the geographical representation 110. By toggling the device-type icons within the panel 140, a user may selectively view one or more types of telepresence devices and disable the display of the other types. Accordingly, a user may filter by telepresence device type.

Additionally, the viewing level 100 may include selectable overlays within an overlay panel 150. The selectable overlays may include, but are not limited to, a population density, a stroke frequency, an adoption rate of a software update, an adoption rate of a firmware update, a frequency of a particular medical condition, a frequency of a particular technical difficulty, an average age of the population, an average age of patients, socioeconomic conditions, an availability of wireless communications, a relative location of medical practitioners, active sessions, a data connection strength, and a relative location of support technicians. The informational overlay may be overlaid on the geographical representation 110 as a heat map, as graphics, as pictures, as icons, as numbers, and/or as text. A user may apply an overlay on the geographical representation 110 in order to visualize the relationships between the information conveyed by the overlay, technical data, healthcare networks, and/or telepresence devices.

A lower panel 160 may include additional selectable icons and/or display information about the current session. For example, a reset icon may allow a user to reset or refresh the visualization and management system. A customer networks icon may allow the user to switch from a geographical representation of the relative location of telepresence devices to a geographical representation of the relative location of healthcare facilities and/or healthcare networks, or to a connectivity control panel.

For purposes of this disclosure, the selection of an icon within any of the panels 130, 140, 150, and 160 may be considered a transition from the viewing level 100 to a different viewing level. Alternatively, the selection of some of the icons within the panels 130, 140, 150, and/or 160 may display additional information, remove displayed information, and/or modify displayed information but remain within the same viewing level. The viewing level 100 illustrated in FIG. 1 may be displayed in a web browser, potentially using one or more plug-ins. Alternatively, the various viewing levels may be displayed and/or controlled in a stand-alone application or in any other suitable computing environment.

Figure 2:
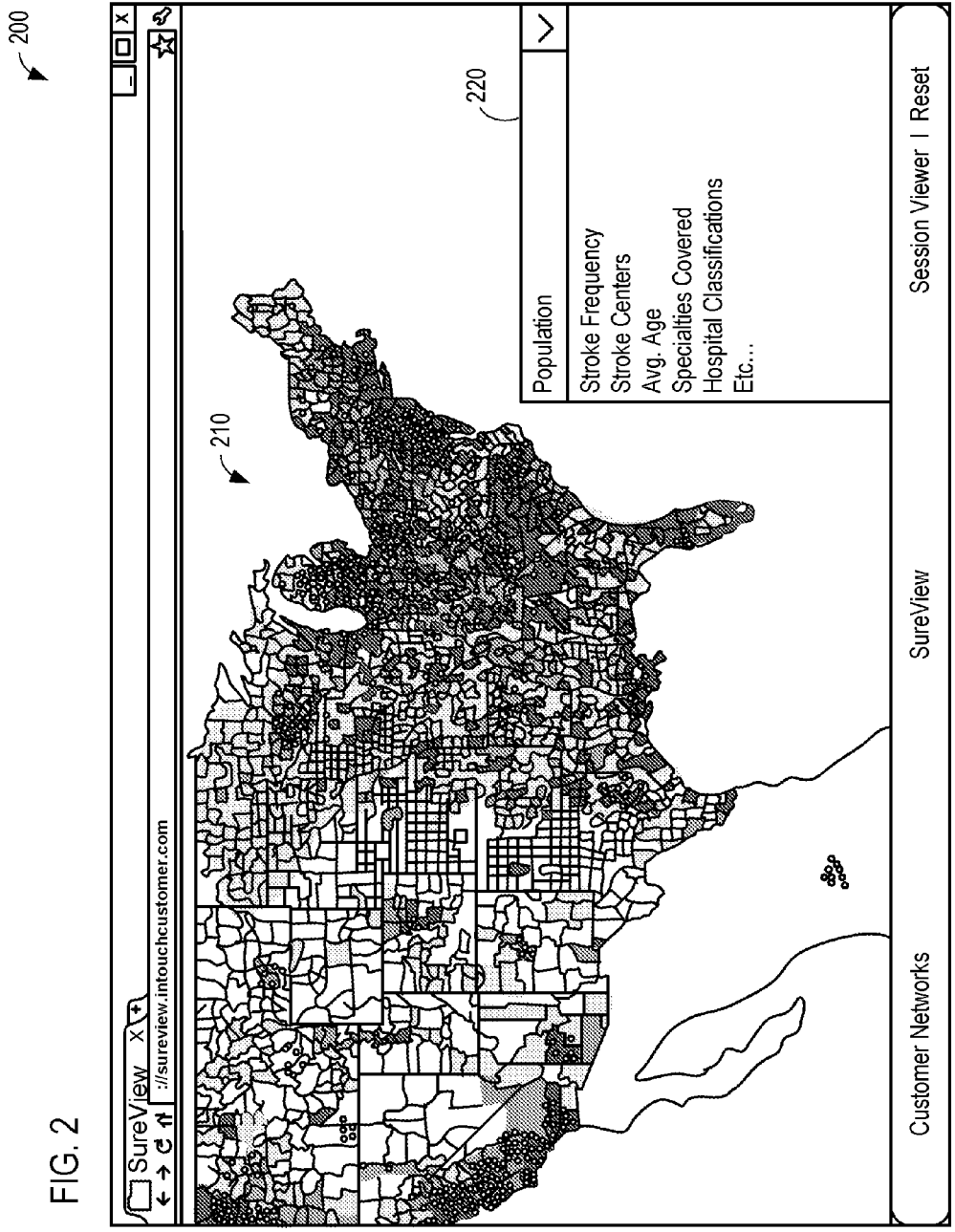
FIG. 2 illustrates a viewing level of a geographical representation of the United States with a population density overlay.

FIG. 2 illustrates a viewing level 200 with a narrower field of view showing a heat map overlaid on a geographical representation 210. The illustrated geographical representation 210 includes the continental United States. As illustrated, an overlay panel 220 may include various informational overlays that may be applied to the geographical representation 210. The overlays may be applied in any of a wide variety of manners, such as by applying a corresponding heat map, graphics, pictures, icons, numbers, and/or text. In the illustrated embodiment, the white dots on the geographical representation 210 may represent available telepresence devices.

The heat map overlay may correspond to a population density. Accordingly, it may be useful (e.g., to assess need or sales opportunities) to compare the population density across the continental United States to the location of available/existing telepresence devices. For instance, in the illustrated example, the population density near the border of Illinois and Iowa is relative high, and yet there is no telepresence device nearby. Accordingly, a sales opportunity or need may exist in that region.

Figure 3:
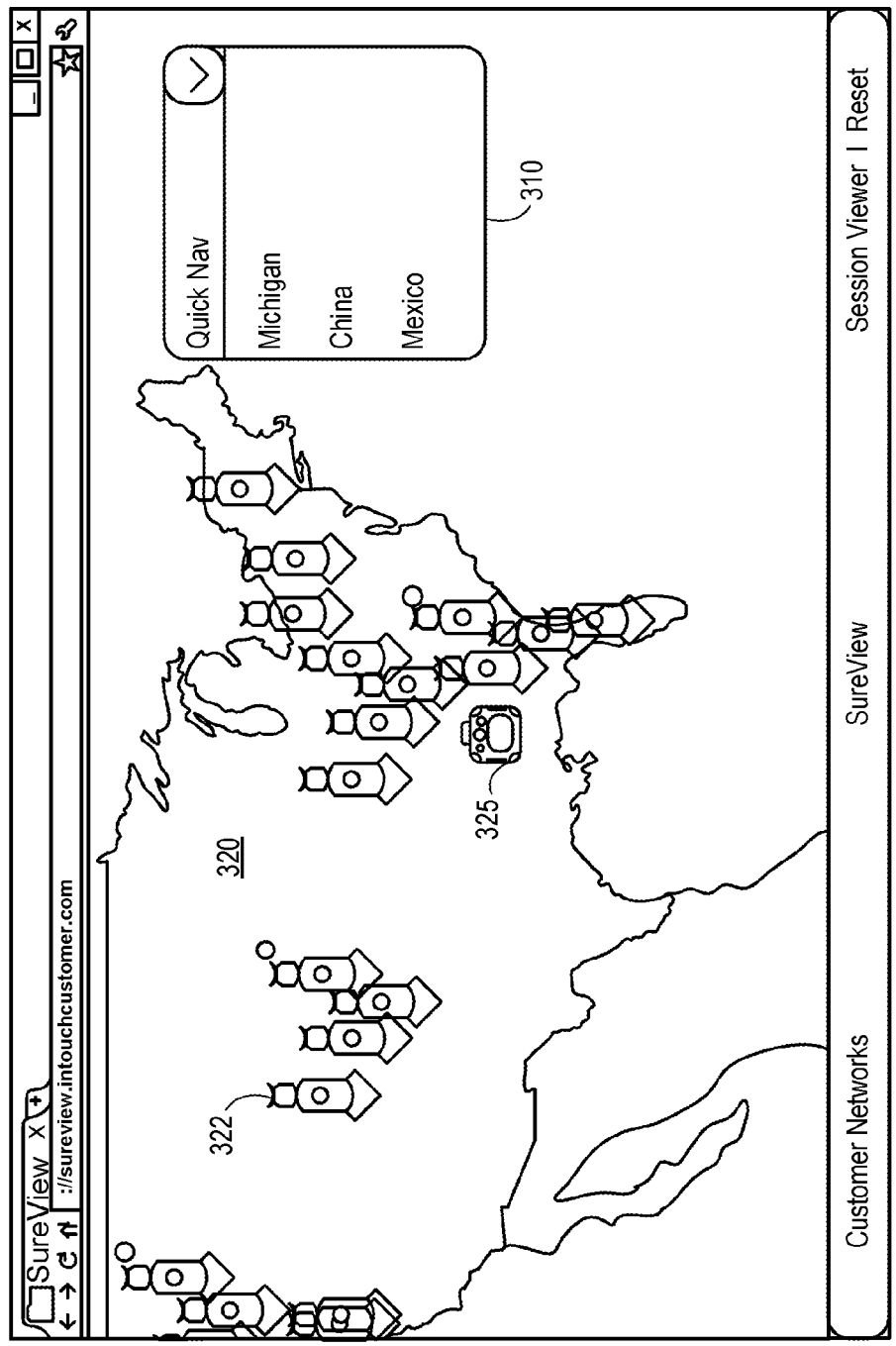
FIG. 3 illustrates a shortcut menu configured to allow for direct navigation to various locations within a geographical representation.

FIG. 3 illustrates a "Quick Nav" shortcut menu 310 configured to allow for direct navigation to a location within the geographical representation 320. The Quick Nav menu 310 may be customized and/or include various default locations. Any number of selectable locations may be included in the shortcut menu 310. Selecting a location within the shortcut menu 310 may pan, rotate, tilt, and/or zoom the window in order to frame the selected geographical location. The telepresence devices and/or healthcare facilities within the framed geographical representation 320 may be displayed as icons resembling corresponding types of telepresence devices and/or healthcare facilities. Alternatively, other symbols, icons, coloring, numbers, text, or markings may be utilized to display the relative location of various telepresence devices and/or healthcare facilities within the displayed geographical boundaries. In the illustrated embodiment, robotically controlled telepresence devices are illustrated with robot icon 322, and mobile telepresence units are illustrated with an icon 325 resembling the device type.

Figure 4B:
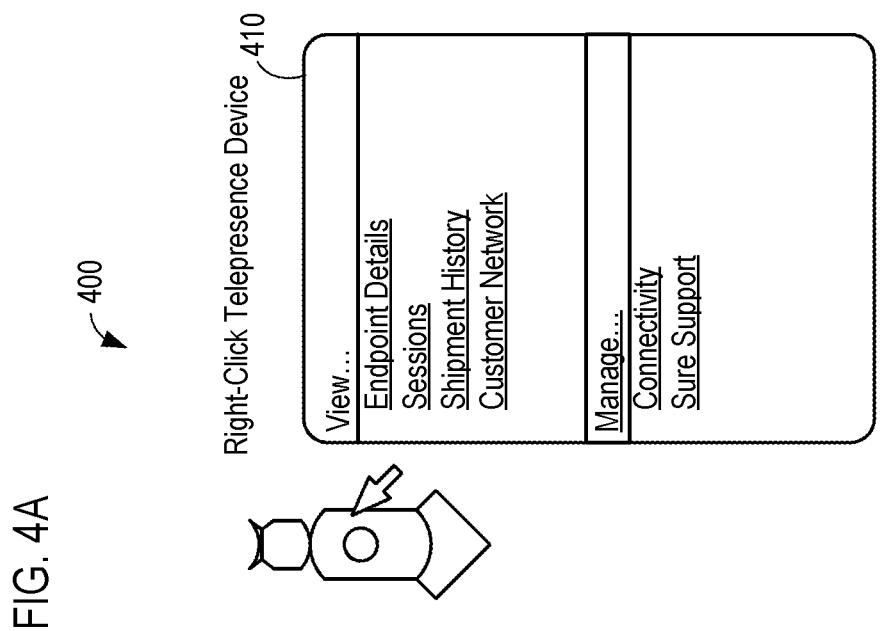
FIGS. 4A and 4B illustrate context-based detail request menus providing access to specific details based on the type of telepresence device and/or type of healthcare facility.
Figure 4A:
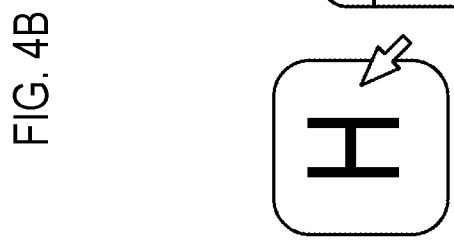

FIGS. 4A and 4B illustrate context-based detail request menus 400 and 450 providing access to specific details based on the type of telepresence device and/or type of healthcare facility. The detailed information, titles, names, and icons used in the menus 400 and 450 may be modified or adapted for a particular application or need. As illustrated in FIG. 4A, by right-clicking (or through the use of another secondary selection method) on the robot icon, a user may select various viewing details or management details in the panel 410. Detail requests may include information associated with telepresence devices, communication sessions, shipment history, and available networks. Additionally, a user may select various management details, such as connectivity and support. Different types of telepresence devices may include different detail selection options for viewing and/or managing. Moreover, the identity of the user may modify which selectable detail requests are available. For example, an administrator of a telepresence device may have more access than a low-level healthcare practitioner.

As illustrated in FIG. 4B, when a healthcare facility icon is right-clicked, a different detail request panel 460 may be displayed. The selectable detail requests within the panel 460 may be based on the identity of the user, a characteristic of the user, the type of healthcare facility, and/or the types of available telepresence devices associated with the healthcare facility. As illustrated, a user may select to view additional details associated with endpoints (telepresence devices) associated with the healthcare facility, connection rules, utilization statistics of telepresence devices, transfer statistics, and other interfacing applications. Additionally, the user may select to manage details such as connectivity, support, and/or a dashboard of other informational details.

Hovering a mouse over a telepresence device icon and/or a healthcare facility icon (a mouse-over) may display one or more details about the specific device/facility. For example, a mouse-over may display the serial number of a telepresence device and the hospital with which it is associated. Additional information may be displayed via a mouse-over and/or by selecting the icon representing the device/facility.

Any of the selectable icons, panels, and/or options may be accessible in any of the viewing levels described herein. Specifically, the viewing level requests via navigation panels and/or shortcut menus (illustrated in FIGS. 1 and 3), the available overlays (illustrated in FIG. 2), and the detail request panels (illustrated in FIGS. 4A and 4B) may be available in the viewing level illustrated in FIG. 1. The exact depictions of icons, panels, geographical representations, and other specific details illustrated and/or described in conjunction with the figures are merely exemplary and may be modified, augmented, replaced, and/or eliminated for a particular application.

Figure 5:
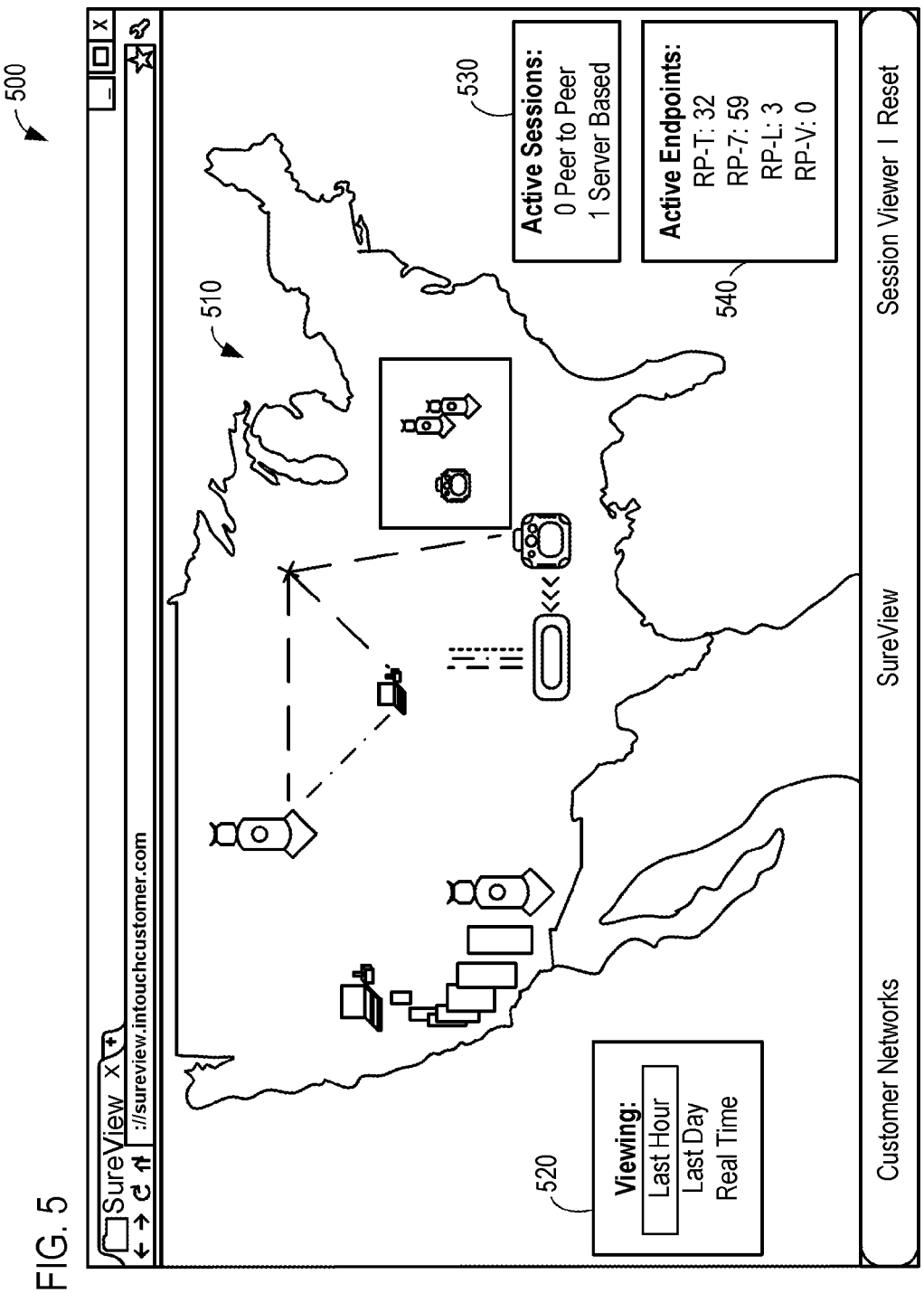
FIG. 5 illustrates a viewing level including a session viewer for monitoring sessions and telepresence devices during a selected time period.

FIG. 5 illustrates a viewing level 500 including a session viewer for visualizing and/or managing sessions and telepresence devices during a selected time period. The session viewer in viewing level 500 may allow a user to visualize data relating to specific remote telepresence sessions on a geographical representation 510. The visualization may include a set of lines or arcs representing the connections. As illustrated, a time period may be selected in the panel 520, the total number of active sessions may be illustrated in the active sessions panel 530, and the active telepresence devices (endpoints) may be illustrated in the panel 540. Icons representing various telepresence devices, healthcare facilities, and/or communication connections may be displayed on the geographical representation 510, as illustrated in FIG. 5.

In various embodiments, visual attributes and/or text associated with the communication connections may be indicative of a telepresence session's quality, control station used, servers used, and/or other session data. For example, the visual appearance of a communication connection may be modified based on the session's quality, the control station, which server was used to negotiate the connection, the endpoint, the type of session (peer-to-peer or server-based), and/or other session data. A single session, a set of sessions from multiple endpoint and control station pairs at a single point in time, and/or a set of multiple sessions over a time span specified by the user may also be provided in this or another viewing level.

In various embodiments, a viewing level including a session viewer as illustrated in FIG. 5 may allow a user to view the number of active sessions, a list of active telepresence devices, and filtering options to limit the types of devices displayed, the connection types, the server types, the time period, and/or other attributes of telepresence sessions. In some cases, a user may view session data associated with a particular mobile telepresence unit. The visualization and management system may display a geographical representation bounded by a travel area of the mobile telepresence unit.

Figure 6:
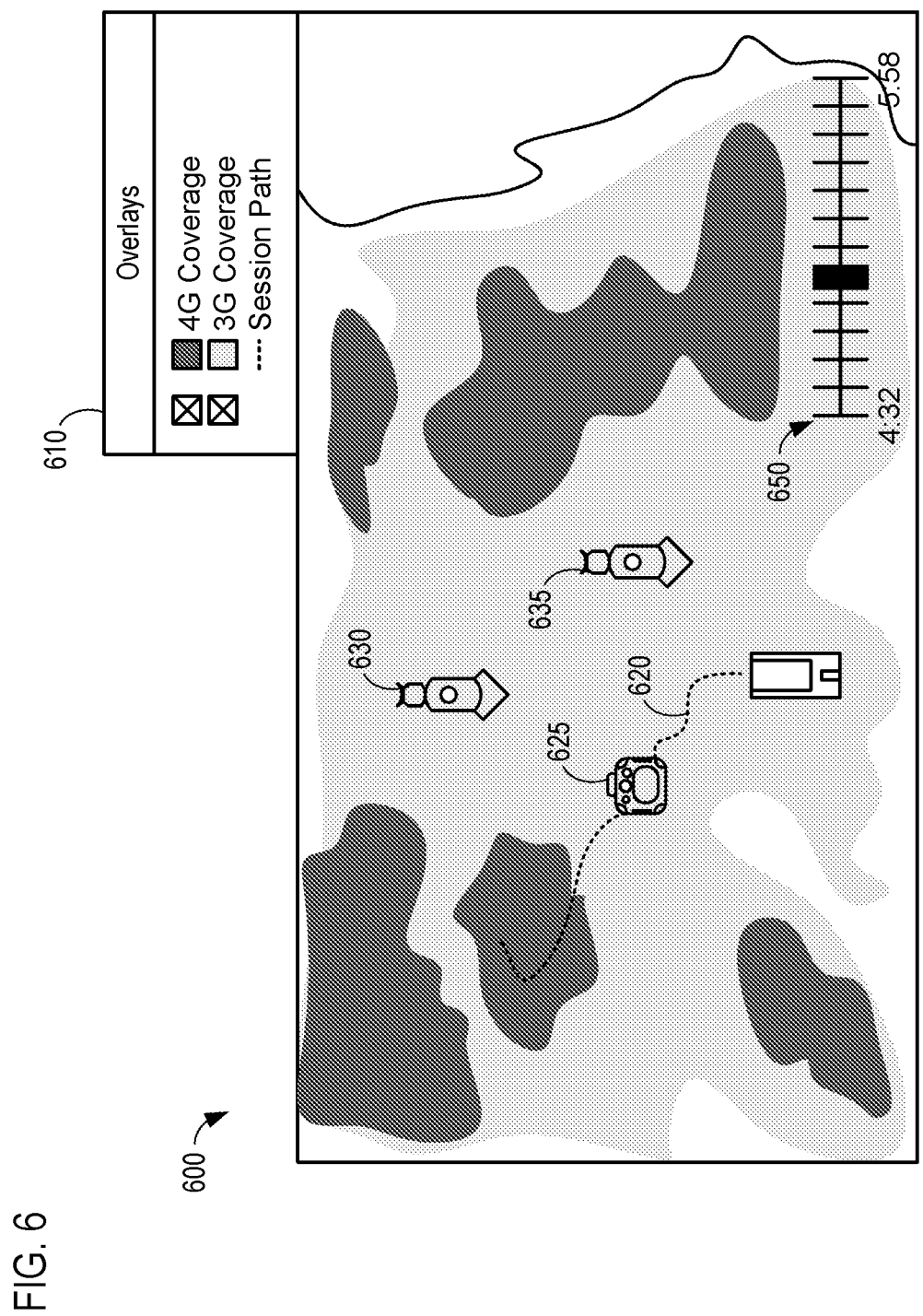
FIG. 6 illustrates a detailed session viewer for monitoring a location of a telepresence device at various time periods on a geographical representation, the geographical representation including an overlay of wireless communication availability.

As illustrated in FIG. 6, various overlays may be used in conjunction with the session viewer viewing level in order to provide additional information about a particular telepresence session. A viewing level 600 may include a route 620 traveled by a mobile telepresence device 625 over a given time period. The viewing level 600 may also include robot telepresence devices 630 and 635 with which the mobile telepresence device 625 communicated. The relative location of the mobile telepresence device 625 may move along the route 620 as the time is moved along the timeline 650 from 4:32 to 5:58 (corresponding to the beginning and end of one or more telepresence sessions).

An overlay, such as 3G and 4G cellular data availability, may be selected from the panel 610 and overlaid on the geographical representation of the viewing level 600 in order to provide additional information to the user. The user may diagnose communication problems and/or improve the overall telepresence session experience using various informational overlays. Such a viewing level may be particularly useful for visualizing and/or managing the use of mobile telepresence units transported in ambulances and/or used remotely by healthcare practitioners (e.g., while at home or on vacation). For example, while monitoring a number of active sessions in a session viewer as illustrated in FIG. 5, a user may see an indication of a connection problem associated with a mobile telepresence device. In response, the user may open a session viewer associated with the mobile telepresence device, as illustrated in FIG. 6, and choose to overlay 3G and/or 4G cellular data availability to investigate and discover possible causes of the connection problem.

Figure 7A:
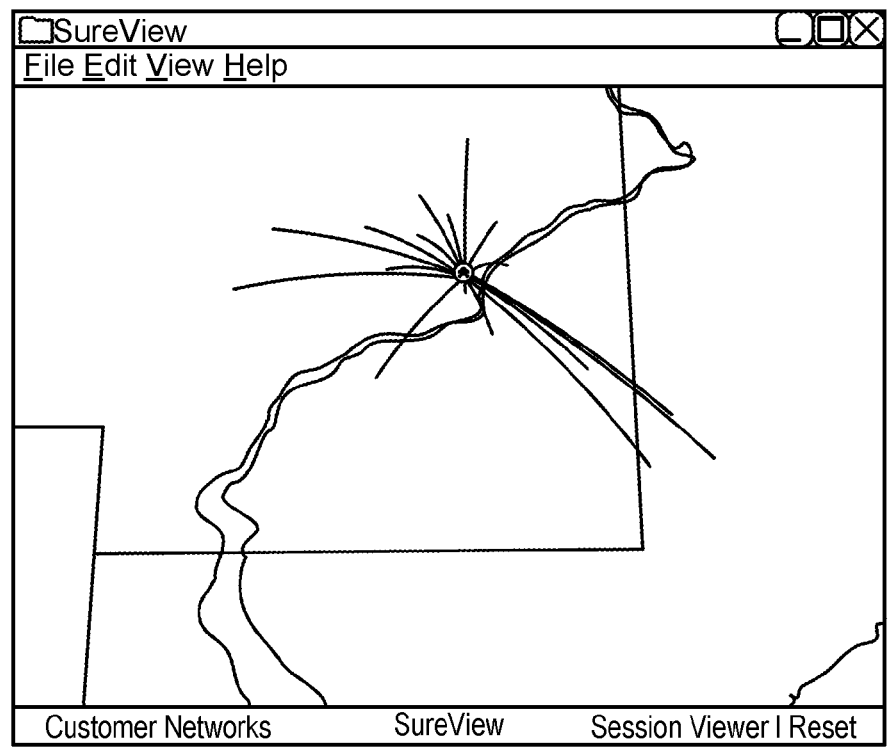
FIGS. 7A and 7B illustrate viewing levels including the location and interconnections of medical facilities in a healthcare network on a geographical representation.

As described in conjunction with FIG. 1, a user may select a viewing level that displays the relative location of at least one healthcare facility and its relationships to other healthcare facilities on a geographical representation. FIG. 7A illustrates a hub healthcare facility, such as a hub hospital, and its relationships with other healthcare facilities as arcs extending from the hub healthcare facility to other related healthcare facilities on a geographical representation. Transitioning to the viewing level 700 may initially remove all telepresence device icons and display a new set of icons representing each customer organization. Different icons may be used to represent each type of healthcare facility and/or the capabilities of each healthcare facility. Additionally, different icons may be used to represent various classes of customers, such as hospitals, clinics, corporate headquarters, partner hospitals, and others. Similar to the description above, hovering over a customer icon may display the organization's name and/or some additional information. Clicking on a customer icon may display all the telepresence devices and/or hospitals associated with the customer's network. Animated arcs representing the current connectivity paths may extend from the customer hub or headquarters to the locations of current telepresence devices.

Figure 7B:
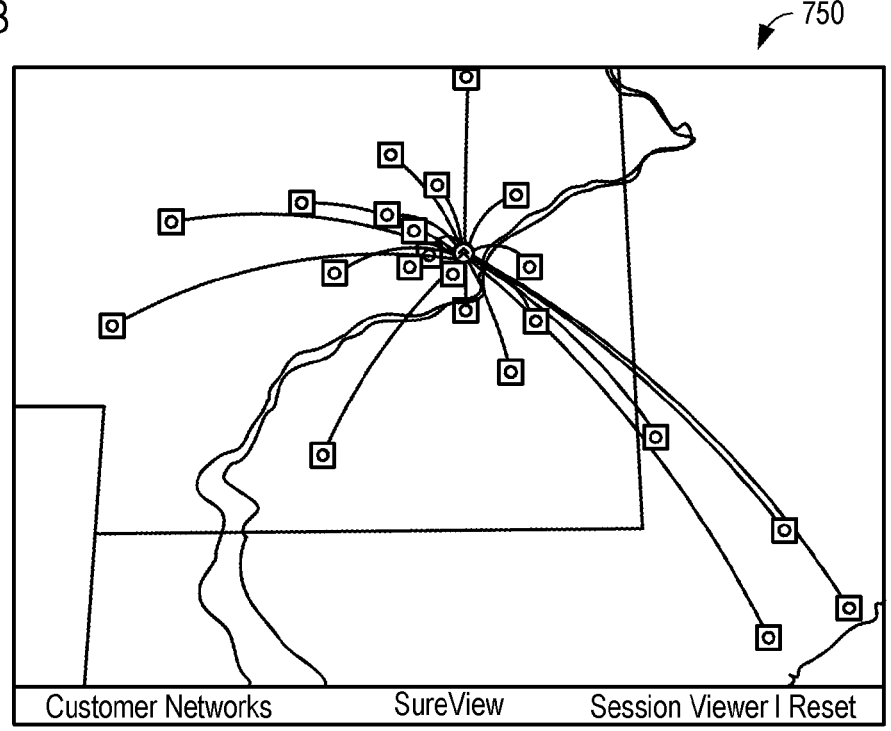

Additional details about arc connections and/or the hub hospital may be made available to a user by selecting or mousing over the icons. FIG. 7B illustrates a viewing level 750 including the location and interconnections of various healthcare facilities in a healthcare network on a geographical representation. Again, context-sensitive detail requests may be made by mousing over the healthcare facilities and/or the connections therebetween.

Additional viewing levels may include menus, icons, and/or other information for visualizing and/or managing the connectivity between various telepresence devices, healthcare practitioners, healthcare facilities, and/or healthcare networks. Additionally, details regarding how and when patients are transferred between various healthcare facilities may be presented as numerical values, as statistics, as graphs, and/or geographically on a geographical representation. In some embodiments, specific viewing levels may be available that display details associated with the shipment history of particular devices and/or software/firmware updates associated with one or more telepresence devices.

For example, a viewing level may include the shipment history of a telepresence device with respect to a timeline. The location of the telepresence device may be visualized at each point during the shipment process. Such a viewing level may allow for the optimization of transportation and shipping of telepresence devices. A viewing level may also be configured to illustrate the progress of an automatic software update from release time to some threshold of acceptance among the telepresence devices in a particular geographical area. For example, a software update is generally released to the entire fleet at a certain time and date. A telepresence device may be automatically updated when it connects to the network. The threshold of acceptance may be when 95% of all telepresence devices have reported that the new update has been installed. The viewing level may provide for the visualization of a software update on a geographical representation. For example, all telepresence devices may initially start with a red circle in their icon to show they have not accepted the update. As the user advances a time bar forward from the release date, the telepresence device icons may change color to show the status of a software update process. This might be from red (not installed) to yellow (downloading from a server) to green (installed). Accordingly, a user may gauge the effectiveness of an automatic software update system. This visualization tool may allow a user to easily identify areas, or specific telepresence devices, where the update process failed or encountered problems.

Figure 8:
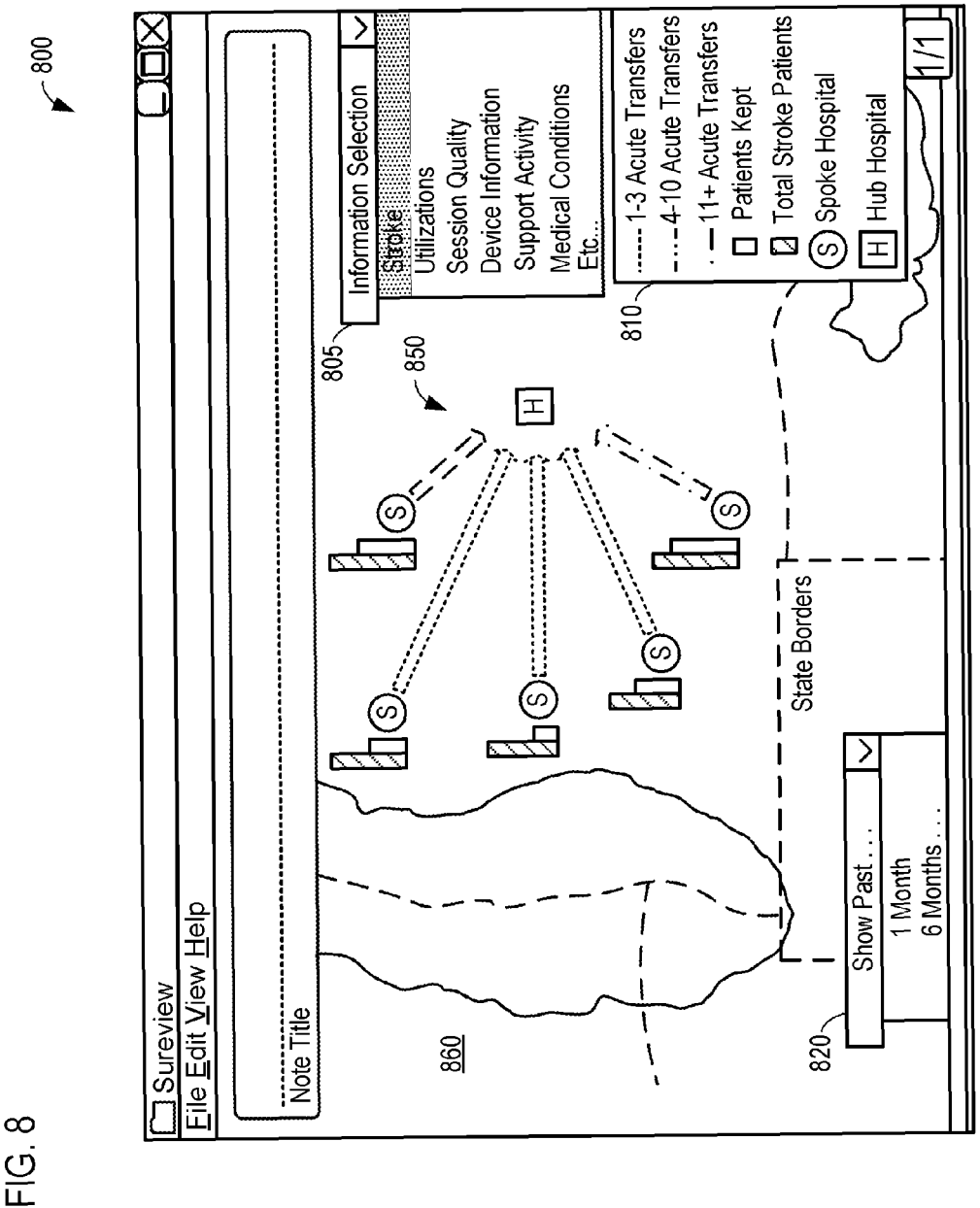
FIG. 8 illustrates a viewing level providing stroke information associated with a healthcare network on a geographical representation.

As illustrated in FIG. 8, a viewing level 800 may display information associated with a healthcare network 850 on a geographical representation 860. A timeline filter may be provided in a panel 820. Viewing level 800 may include an information selection panel 805. The viewing level 800 allows information from panel 805 that is associated with multiple healthcare facilities and/or telepresence devices shown in a key 810 to be visually presented in conjunction with a geographical representation 860. A user may select between a variety of informational overlays, graphs, informational tags, icons, text, numbers, connection lines, and/or colors to visually convey information related to healthcare facilities and/or telepresence devices. According to various embodiments, a user may graphically compare data among spoke healthcare facilities or between spoke healthcare facilities and a hub healthcare facility (see the key 810) on the geographical representation 860.

In the illustrated embodiment, stroke information has been selected in the information selection panel 805. Accordingly, a user may view the number of patients who were the subject of a stroke consultation made by a healthcare practitioner in a hub healthcare facility using telepresence devices. A user may view the number of such patients who were determined fit to stay in the rural (spoke) healthcare facilities, and those who were transferred to the more capable hub healthcare facility. Such a viewing level may allow for a visualization of the effectiveness and results of consultations via telepresence devices.

The viewing level 800 may allow a user to visualize the value a telepresence system is bringing to a customer's hub hospital and spoke hospitals in terms of patients kept and acute cases transferred. For example, a rural hospital's administrator may visualize the number of patients who were subject to a telepresence consultation performed by a specialist based in a hub hospital. The rural healthcare facility may have a small graph beside it indicating the number of patients kept versus the total number of stroke patients admitted in the selected time period. The healthcare facility may also have an arrow configured with a width corresponding to the relative number of patients transferred from the spoke healthcare facility to the hub healthcare facility. Accordingly, the rural hospital administrator (and the hub hospital administrator) may visualize the benefits of the telepresence devices and telepresence network.

The user may select a different information set from the information selection panel 805 in order to visualize data relating to a particular facility or device, or visually compare data between and/or among various spoke and hub healthcare facilities on the geographical representation 860. Additionally, information directly related to the telepresence devices may be selected within information selection panel 805, in order for a user to visually compare the status of telepresence devices between spoke healthcare facilities on the geographical representation 860. Information sets selectable via the information selection panel 805 may include, but are not limited to, information related to medical condition, such as stroke or heart attack, utilization rates, session quality information, telepresence device information, support activity, battery levels, last reported time, active session, workflow metrics, available telepresence devices, trained specialists, financial information, subscription information, and/or other information associated with telepresence devices, telepresence networks, healthcare facilities, and/or healthcare networks.

Figure 9:
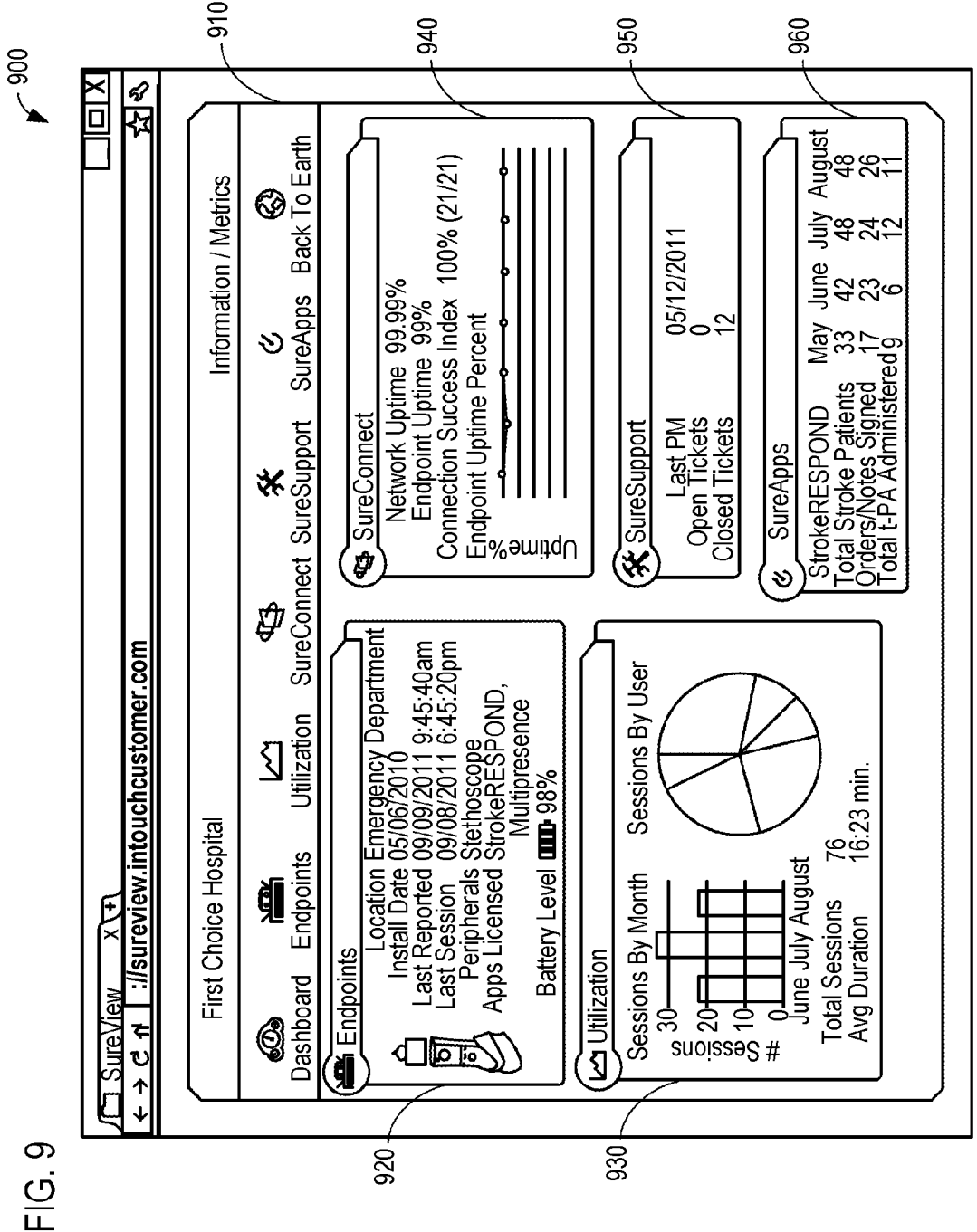
FIG. 9 illustrates a viewing level including a dashboard of detailed information associated with one or more telepresence devices.

FIG. 9 illustrates a viewing level 900 including a dashboard of detailed information 920, 930, 940, 950, and 960 associated with one or more telepresence devices. The displayed details may include various numerical information, charts, and/or graphs. The information displayed in the dashboard of information may depend on the types of telepresence devices, the types of healthcare facilities, and/or the identity of the user. A navigation bar 910 may allow the user to navigate between various viewing levels. In the illustrated example, an endpoints panel 920 may include details associated with one or more endpoints (telepresence devices) in a healthcare facility. The endpoints panel 920 may include real-time information associated with a particular telepresence device, including, but not limited to, serial number, model number, type, name, battery level, connection status, location, date and time last reported, available peripherals, and associated applications.

A utilization panel 930 may display details associated with the remote telepresence sessions for one or more telepresence devices and/or a particular healthcare facility or network. For example, the utilization panel 930 may include details regarding utilization over various time periods, a total utilization time, an average session duration, a duration of a particular session, a start time and end time of a particular session, a Quality of Service (QoS) for one or more sessions, a current available bandwidth, a bandwidth availability with respect to time, a current location of a telepresence device, and historical locations of a telepresence device with respect to time.

A support panel 950 may display information associated with technical support, software updates, firmware updates, hardware updates/replacements, and/or other support issues. The support panel 950 may display a list of personnel responsible for a telepresence device and/or healthcare facility. Historical data regarding support issues may also be available. Automatic and/or manual updates may be applied via support panel 950 as well.

An application panel 960 may provide information associated with applications registered for use with the telepresence device and/or healthcare facility. Information associated with various workflow applications, such as StrokeRESPOND described in U.S. patent application Ser. No. 12/362,454, filed on Jan. 29, 2009, titled "DOCUMENTATION THROUGH A REMOTE PRESENCE ROBOT," which application is hereby incorporated by reference in its entirety, may also be displayed or made accessible in application panel 960.

A connection panel 940 may include information associated with network connections and maintenance. For instance, the connection panel 940 may display the basic network start and end times and durations of network connectivity. The connection panel 940 may include a graphical representation of network up-time, network down-time, bandwidth availability, bandwidth use, max ping, average ping, packet loss, and/or other information associated with network connectivity between a telepresence device and a healthcare facility. Network information associated with a connection between two healthcare facilities may also be displayed and/or managed.

The connection panel 940 may additionally, or alternatively, display information associated with connection services configured to provide a reliable and robust peer-to-peer and/or server-based connection across a wide range of network types. For instance, the systems and methods described in U.S. patent application Ser. No. 11/801,491, filed on May 9, 2007, titled "ROBOT SYSTEM THAT OPERATES THROUGH A NETWORK FIREWALL," which application is hereby incorporated by reference in its entirety, may be used in conjunction with the presently described systems and methods. The connection panel 940 may also display information associated with automatic bandwidth tests and/or general profiling of a network.

Figure 10:
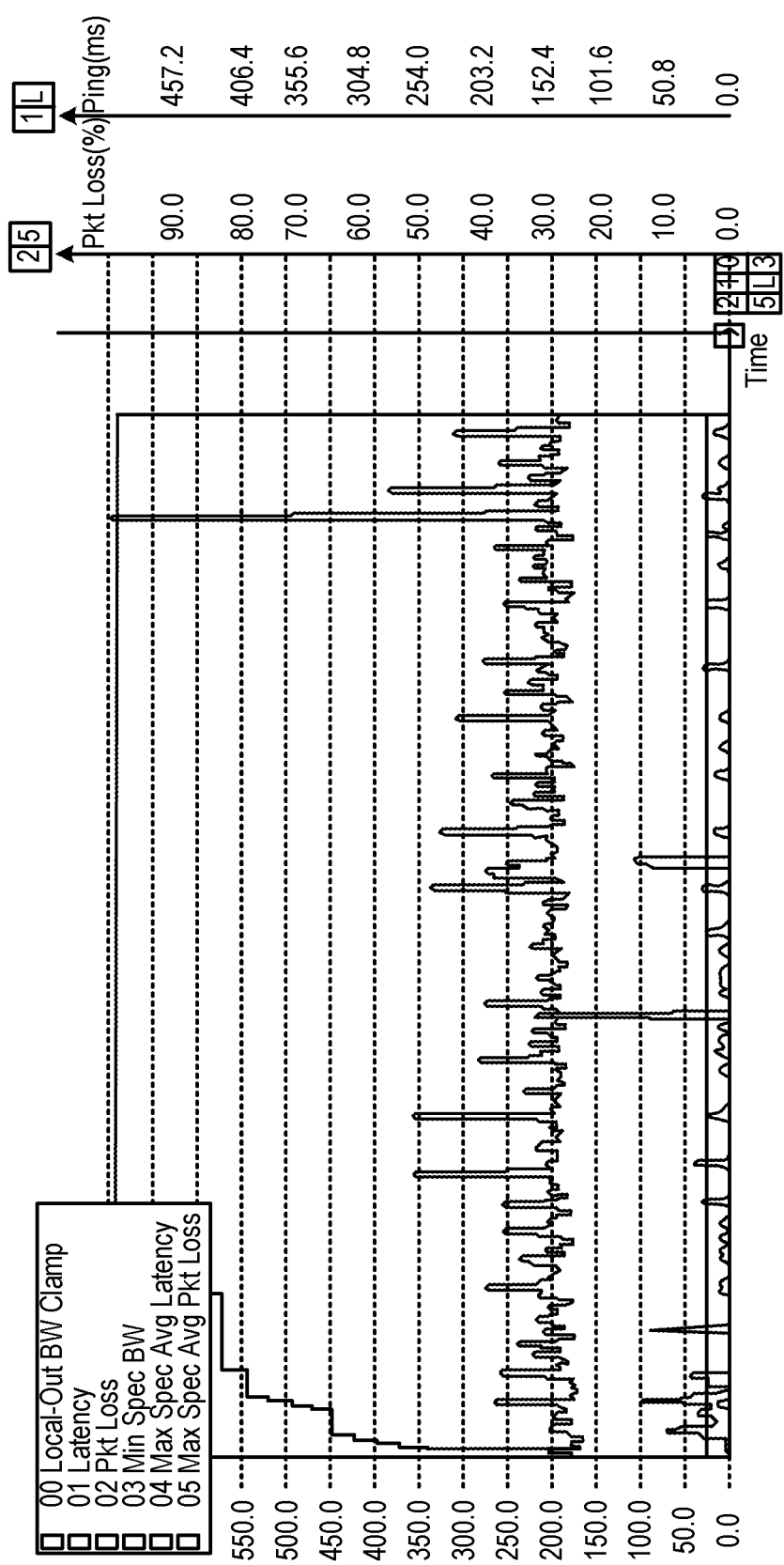
FIG. 10 illustrates a viewing level including session details for a particular telepresence device.

FIG. 10 illustrates a viewing level 1000 displaying the dynamic bandwidth management, latency, and packet loss during various time periods for one or more telepresence devices. Such a viewing level 1000 may be useful for a user to diagnose networking problems and/or improve a telepresence network.

Figure 11:
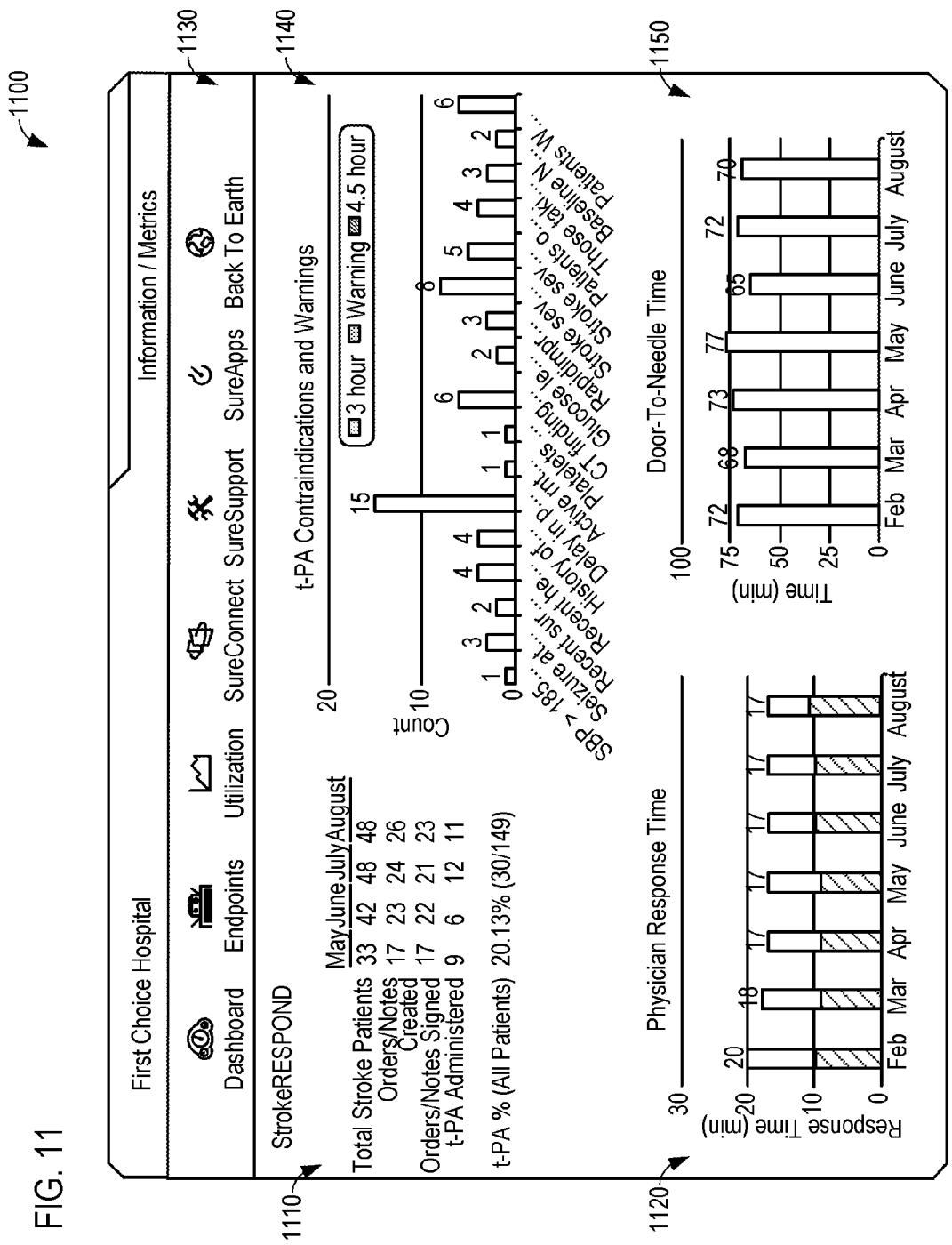
FIG. 11 illustrates a viewing level including stroke information associated with a healthcare network provided via a StrokeRESPOND application.

FIG. 11 illustrates a viewing level 1100 of an application selected via the application panel 960 in FIG. 9. The exemplary information panels illustrated in FIG. 11 are associated with the application StrokeRESPOND. Any of a wide variety of application interfaces may be accessible via the visualization and management system described herein. As illustrated, information associated with strokes may be displayed in conjunction with the StrokeRESPOND application. For instance, the display may include a door-to-needle time 1150 corresponding to the amount of time between a patient's arrival at a healthcare facility and the time the patient receives clot-busting medication. The display may also include StrokeRESPOND statistics 1110, physician response times 1120, and/or t-PA contraindications and warning information 1140. A user may navigate to alternative viewing levels and/or return to the previous viewing level via the panel 1130.

Figure 12:
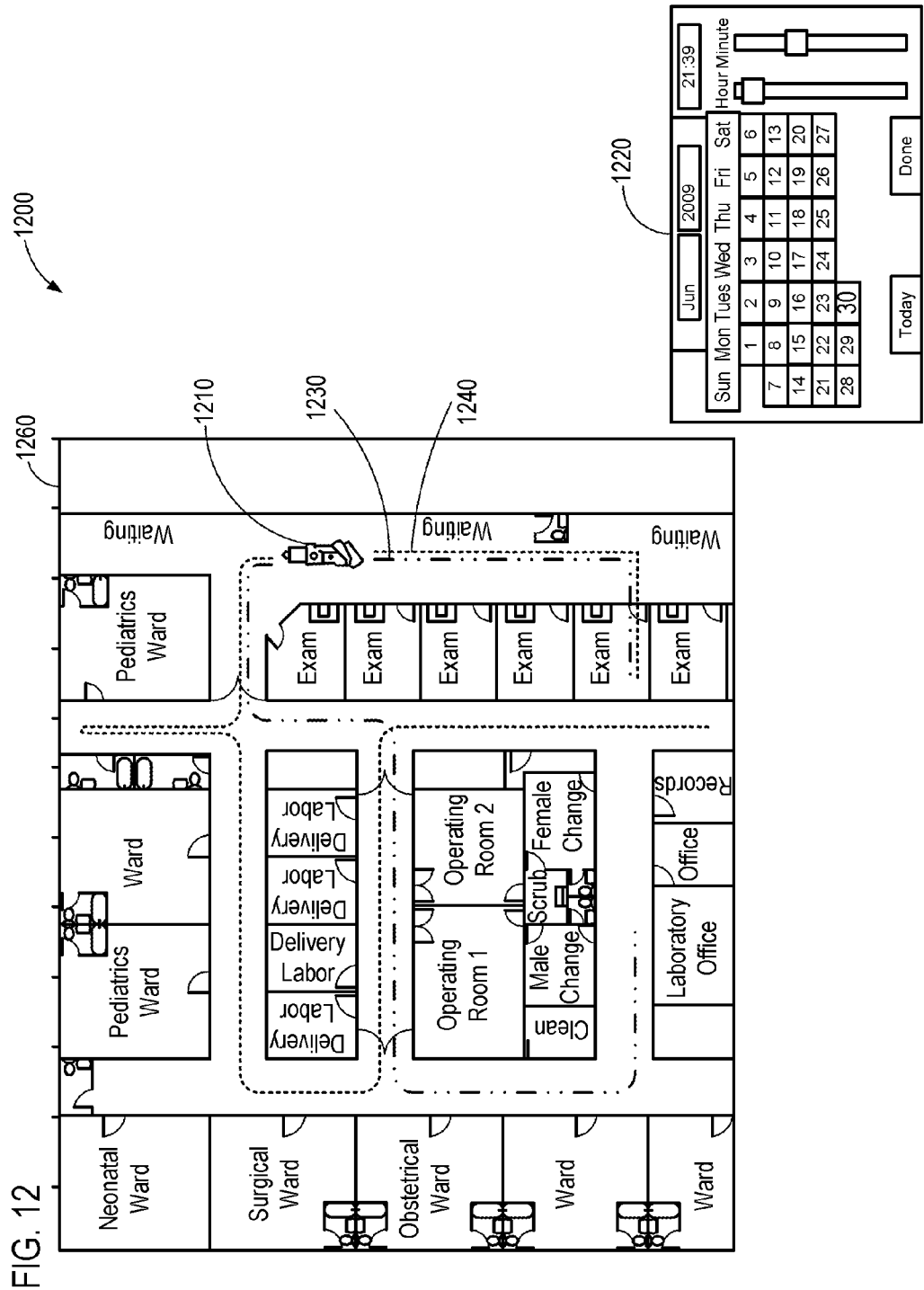
FIG. 12 illustrates a viewing level showing navigational paths of a telepresence device on a plan map for a selected time period.

FIG. 12 illustrates a viewing level 1200 showing the navigational paths 1230 and 1240 of a telepresence device 1210 on a plan map 1260 for a selected time period. According to various embodiments, the viewing level 1200 may be selected via the application panel 960 in FIG. 9, from within the detail request panel 460 of FIG. 4B, and/or from within any other viewing level. The viewing level 1200 may be selected based on a particular healthcare facility or based on a particular telepresence device 1210. In some embodiments, the viewing level 1200 showing the navigational paths 1230 and 1240 may be an independent program, application, or accessible website.

As illustrated, the plan map 1260 may include various hallways and rooms of a healthcare facility. In some embodiments, the number of rooms, hallways, and/or floors may justify a zoom selection tool, a panning selection tool, and/or a floor selection tool. According to various embodiments, the plan map 1260 may be displayed along with a time period selection menu 1220. A user may select a time period via the time period selection menu 1220. According to various embodiments, the time period may range from a few minutes to a few days. In the illustrated embodiment, a user may select a day from a calendar and a time from a slider bar. The user-selected time may constitute a lower bound of a selected time period. The upper bound may also be selected by the user, or, as illustrated, the upper bound may be the current date and time.

Navigational paths 1230 and 1240 of the telepresence device for the selected time period may be displayed on the plan map 1260. The visualization tool in viewing level 1200 may provide a user with a useful ability to distinguish between a navigational path 1230 in which the telepresence device 1210 was in a teleoperated drive mode, and a navigational path 1240 in which the telepresence device 1210 was in an autonomous drive mode. Additional drive modes, such as a hybrid drive mode, may also be distinguishable on the plan map 1260. Descriptions of various drive modes and systems and methods for implementing the same are described in U.S. patent application Ser. No. 13/360,579, filed on Jan. 27, 2012, titled "INTERFACING WITH A MOBILE TELEPRESENCE ROBOT," which application is hereby incorporated by reference in its entirety.

In the illustrated embodiments, the navigational path 1230 in which the telepresence device 1210 was in a teleoperated drive mode is illustrated as a dashed line and the navigational path 1240 in which the telepresence device 1210 was in an autonomous drive mode is illustrated as a dash-dot-dot line. In practice, the navigational paths 1230 and 1240 representing different drive modes may be illustrated on the plan map 1260 as different colors, shades, line patterns, opacities, etc. In addition, intersections of multiple types of navigational paths 1230 and 1240 may be displayed side-by-side (as illustrated) or as a third line color, a particular line shading gradient, a line thickness, a line pattern, or a line hue. For example, if the navigational path 1230 in which the telepresence device 1210 was in a teleoperated drive mode is displayed as a red line and the navigational path 1240 in which the telepresence device 1210 was in an autonomous drive mode is illustrated as a blue line, the intersections of the two lines may be illustrated as purple lines. Such intersections may include long sections of hallways or rooms that the telepresence device 1210 traversed in more than one drive mode.

Additionally, the number of times the telepresence device 1210 traversed a particular section of the plan map 1260 may be displayed as well. For example, the thickness of a displayed navigational path may correspond to the number of times the telepresence device 1210 traversed the navigational path. In other embodiments, the number of times the telepresence device traversed a particular section of a navigational path in a particular drive mode may be visualized using various line colors, line shading gradients, line color gradients, line thicknesses, line patterns, line hues, numerical annotations, and/or symbolic annotations.

In some embodiments, the current location of the telepresence device 1210 may be displayed on the plan map 1260. In other embodiments, the location of the telepresence device may be displayed at a selected instantaneous time, displayed at an upper or lower bound of a selected time period, or selectively removed from display.

Figure 13:
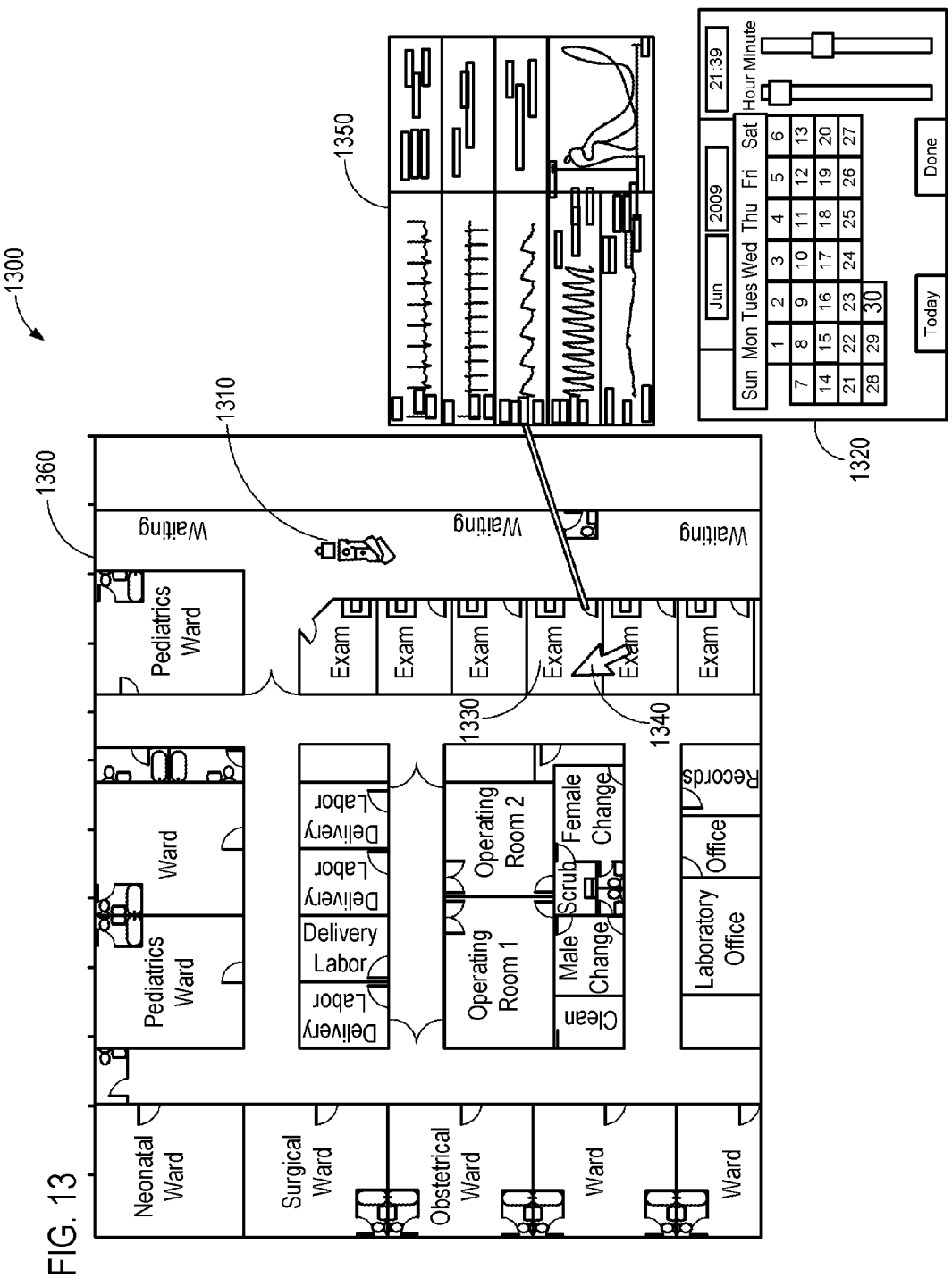
FIG. 13 illustrates a viewing level showing telemetry data for a patient as a pop-up window on a plan map in a selected room of a healthcare facility.

FIG. 13 illustrates a viewing level 1300 allowing a user to visualize telemetry data 1350 for a patient as a pop-up window on a plan map 1360 in a selected room 1330. Again, the viewing level 1300 may be selected via the application panel 960 in FIG. 9, from within the detail request panel 460 of FIG. 4B, and/or from within any other viewing level. The viewing level 1300 may be selected based on a particular healthcare facility or based on the telepresence device 1310. In some embodiments, viewing level 1300 may be an independent program, application, or accessible website.

As illustrated, the plan map 1360 may include various hallways and rooms of a healthcare facility. In some embodiments, the number of rooms, hallways, and/or floors may justify a zoom selection tool, a panning selection tool, and/or a floor selection tool (not illustrated); such navigation features may be added as is deemed useful for a particular application. According to various embodiments, the plan map 1360 may be displayed along with a time period selection menu 1320. A user may select a time via the time period selection menu 1320. In the illustrated embodiment, a user may select a day from a calendar and a time from a slider bar. Additionally, a user may select a room within the plan map 1360.

Telemetry data 1350 for a patient within the selected room at the selected time may be displayed as a pop-up window (or as a standalone window). The telemetry data 1350 may be collected and recorded by various monitoring and data collection systems, including the telepresence device 1310. The telemetry data 1350 may include data such as blood pressure, heart rate, temperature, respiration rate, and electrocardiogram information. The displayed telemetry data 1350 may be instantaneous telemetry data for the selected time. For example, the telemetry data may be displayed as instantaneous numerical values. The displayed telemetry data 1350 may include waveforms plotted over time. In such an embodiment, the waveform may include, begin with, be centered on, or end with the selected time.

A user may select a room in any of a wide variety of ways. For example, a user may select a room via a mouse-over 1340 held over the room 1330 for a predetermined amount of time. In alternative embodiments, mouse clicks, keyboard inputs, touch inputs, and/or other auxiliary selection inputs may be used to select a room on the plan map 1360.

In some embodiments, the viewing level 1300 of FIG. 13 and the viewing level 1200 of FIG. 12 may be combined into a single viewing level. In such an embodiment, a user may selectively view navigational paths of a telepresence device and/or telemetry data associated with a patient within a particular room.

FIG. 14 illustrates a table 1400 of patients and various associated data. Some of the various data points associated with each patient may be omitted, or additional data points may be included. In some embodiments, the table 1400 may be displayed directly to a user. Visualization of the data in table 1400 may be further enhanced using the visualization tools illustrated in FIGS. 15-20. The actual data within each category and the number of patients is merely exemplary. The data within each category may vary by hospital, by physician(s), by telepresence device, and/or by individual experiences. Moreover, larger data sets may more accurately reveal trends in the data. The data categories are described below from left to right across FIG. 14.

The table 1400 includes a patient identification 1401. The patient identification may be a name, a number, an alphanumeric string, or a pseudonym, and may identify gender, etc. Each patient may be ranked or assigned an outcome rating 1402. The outcome rating may be assigned automatically based on a predefined set of criteria, or may be input by a nurse, doctor, or other medical practitioner. The outcome rating may be a daily rating, an average rating for a given time period, or an outcome rating for a discharged patient. In one example, the outcome rating corresponds to a practitioner-assigned rating given to each patient as the patient is discharged. In one embodiment, the outcome rating is a numerical value ranging from 0 (death) to 100 (full recovery). Ratings between 0 and 100 may be subjective or objectively assigned based on a predetermined set of criteria.

The data may include a primary physician 1403. The primary physician may be the primary physician assigned to the patient at a time the outcome rating was assigned, or the primary physician of the patient based on the total amount of time a physician cared for the patient. In some embodiments, a patient may have a local primary physician and a remote primary physician. The primary physician 1403 listed on the table 1400 may be the physician who most used the telepresence device to treat the patient. The data may include a primary condition 1404 as well. The primary condition 1404 may be a general category describing the condition for which the patient is being treated. In some embodiments, the patient may have multiple primary conditions 1404.

The data may also include a room number 1405 of the patient and the number of visits made each day by a telepresence device 1406. Information about the usage of a telepresence device accessory, such as the number of times a stethoscope of the telepresence device is used 1407, may also be included. Telepresence device accessories may include any of a wide variety of accessory devices configured to measure a physiological parameter. Measuring a physiological parameter may include a remote practitioner viewing a sonogram screen as a sonogram device is used on a patient. Additional examples of accessories that may be used via a telepresence device include accessories configured to determine blood pressure, heart rate, temperature, respiration rate, and electrocardiogram information. Any of a wide variety of instruments and visualization tools may be incorporated as accessories to a telepresence device, and the usage of the same may be included as data points in the table 1400.

Information associated with camera usage may also be included. For example, the amount of time a camera of the telepresence device is zoomed to 50% or greater 1408, the amount of time the camera of the telepresence device is used to look at the patient 1409, the amount of time the camera of the telepresence device is used to look at staff for the patient 1410, the amount of time the camera of the telepresence device is used to look at a monitor for a patient 1411, and/or the amount of time the camera of the telepresence device is used to look at charts for the patient 1412 may be included in table 1400. The data may also include the amount of time the camera of the telepresence device is used to look at other things 1413. Whether the camera of the telepresence device is being used to look at a patient, a family member, staff, charts, monitors, or other things could be determined using one or more image analysis or computer vision techniques. For example, this functionality could be accomplished using Haar-like feature detection to identify faces. Patients, who may be in a prostrate position, may be distinguished from family and staff using height or skeletal mapping to identify probable body position. Additionally, feature detection algorithms such as scale-invariant feature transform (SIFT) may be used to identify hospital attire for distinguishing hospital personnel. SIFT-based feature detection may also be used to identify screens and charts.

The data may also include the amount of time the telepresence device is in the room of the patient 1414, the amount of time the telepresence device is at the bedside of the patient 1415, and/or the amount of time the telepresence device spends driving 1416. This data may be filtered such that the amount of time the telepresence device is in the room does not include the amount of time the telepresence device is at the patient's bedside, even though the telepresence device was necessarily within the patient's room when it was at the patient's bedside.

An analysis of the data above may also enable a user to discover usage trends for a telepresence device that result in the most positive outcome ratings. For example, it may be discovered that the number of visits by a telepresence device per day correlates to positive patient ratings. The following description of FIGS. 15-20 illustrates various examples of potential visualization parameters that allow for the data of numerous patients to be visually presented in a useful manner to a user. It may be appreciated that an exhaustive table of thousands of patients may be difficult for a user to process. However, a graphical visualization tool may allow a user to quickly discover correlations and associations between the usage of a telepresence device and patient well-being.

Figure 15:
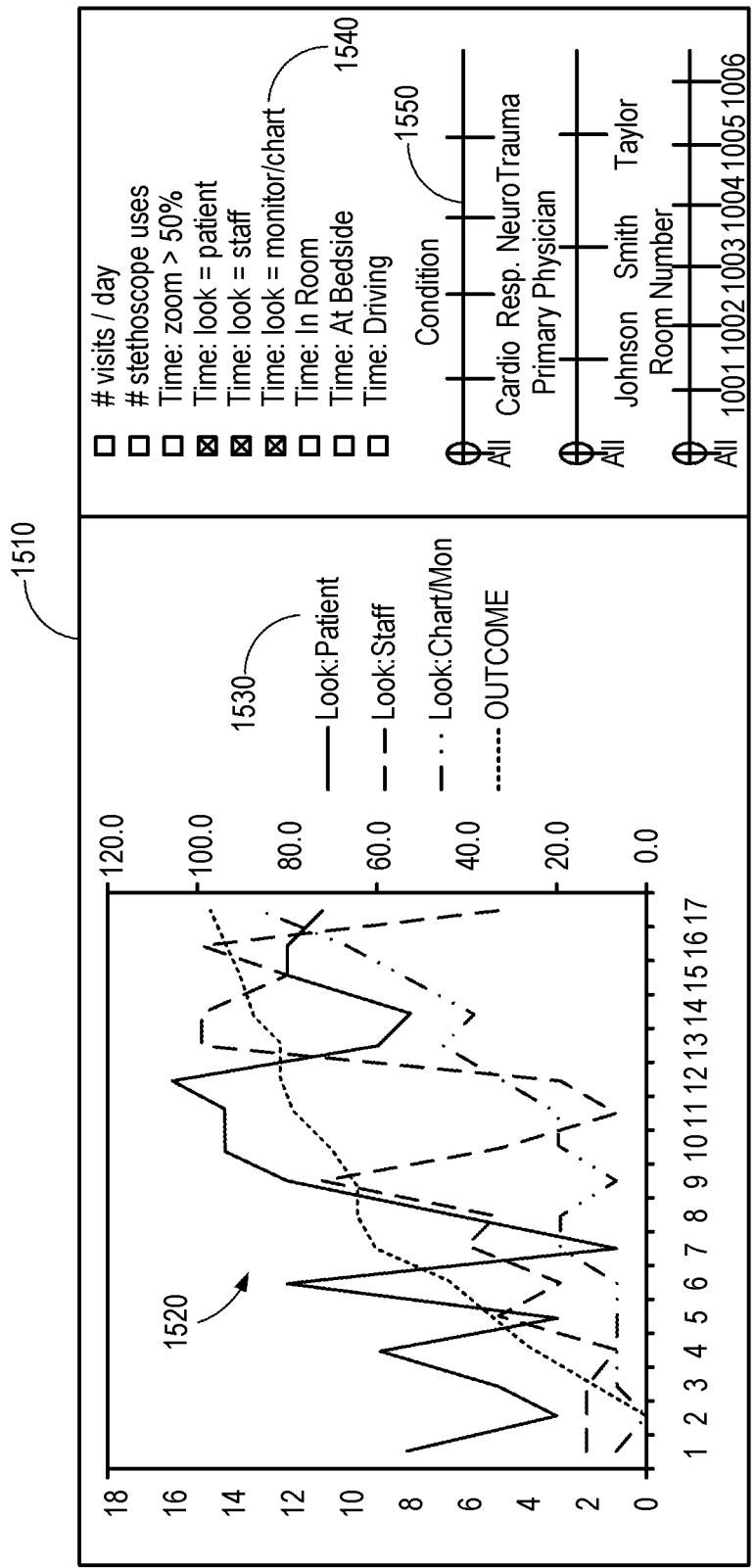
FIG. 15 illustrates a coordinate system including selected graphs of patient outcome ratings and various telepresence device statistics.

FIG. 15 illustrates a coordinate system 1510 including selected graphs 1520 of patient outcome ratings and various telepresence device statistics associated with the patients. As illustrated, the viewing level 1500 includes the coordinate system 1510, with various graphs 1520, and a legend 1530. The horizontal axis of each of the coordinate systems in FIGS. 15-20 is labeled with the identification numbers of each of a plurality of patients. Accordingly, graphs 1520 are graphed with respect to each patient. In some embodiments, the graphs may be graphed as scatterplots, accurately reflecting the discrete number of patients. In other embodiments, line graphs may be extrapolated from the available data, and/or another type of graph, such as a bar graph, may be utilized.

Viewing level 1500 may further include a telepresence device statistic selection panel 1540 allowing a user to selectively display graphs for any number of telepresence device statistics.

The telepresence device statistics may include any of a wide variety of informational data associated with the usage of a telepresence device for a particular patient. In the illustrated embodiments, the selectable telepresence device statistics include (from top to bottom) the number of visits made by the telepresence device per day, the number of stethoscope usages during a certain time period (it may be the entire time the patient was being treated), the amount of time a camera of the telepresence device is zoomed to 50% or more, the amount of time the camera of the telepresence device is used to look at a patient, the amount of time the camera of the telepresence device is used to look at staff, the amount of time the camera of the telepresence device is used to look at monitors or charts, the amount of time the telepresence device is in the patient's room, the amount of time the telepresence device is at the patient's bedside, and the amount of time the telepresence device is driving for the patient. Additional telepresence device statistics may be included in the telepresence device statistic selection panel 1540, and/or some of the listed statistics may be omitted. Similar abbreviations for the various telepresence device statistics 1540 are used throughout FIGS. 15-20. A filter selection panel 1550 is set to "all" in FIG. 15.

FIG. 15 illustrates a coordinate system 1510 including selected graphs 1520 corresponding to the checked boxes in the telepresence device statistic selection panel 1540. The graphs 1520 indicate that the amount of time a camera of a telepresence device is used to look at monitors/charts may correspond to the outcome ranking of a patient. It will be appreciated that similar data in a table form may be difficult to analyze for a user, while the visualization techniques and tools described herein may facilitate rapid and improved data analysis in a selective graphical form.

Figure 16:
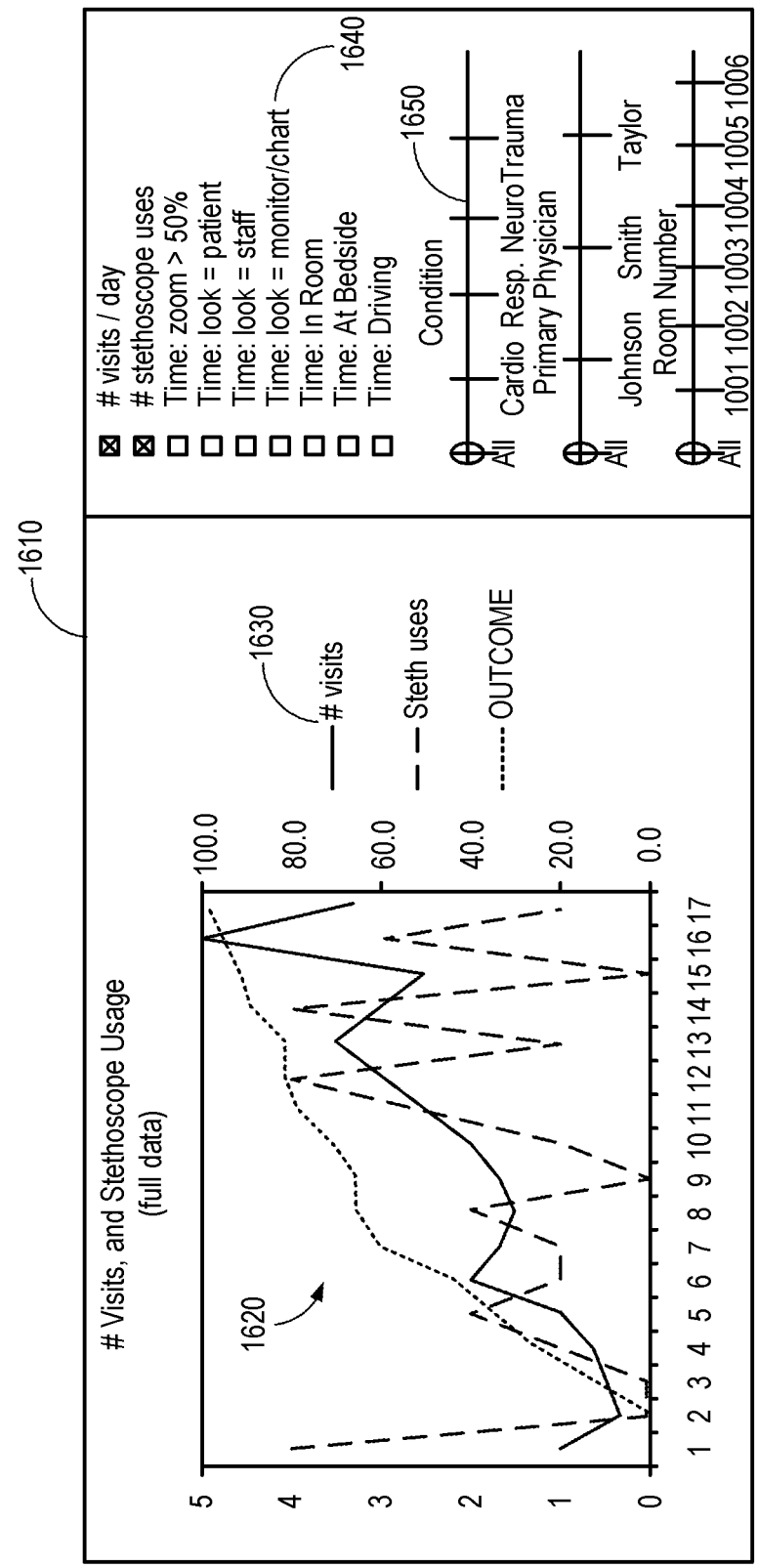
FIG. 16 illustrates a coordinate system including graphs of patient outcome ratings, a number of visits per day, and a number of stethoscope uses.

FIG. 16 illustrates viewing level 1600 including a coordinate system 1610 with a number of selected graphs 1620, including an outcome rating for each patient, the number of visits by a telepresence device each day to each patient, and the number of stethoscope usages for each patient. A legend 1630 may facilitate review of the coordinate system 1610. In the illustrated examples, graphs 1620 are distinguishable based on different line patterns (dashes). In practice, each graph 1620 may be distinguishable using various line colors, line shading gradients, line color gradients, line thicknesses, line patterns, line hues, numerical annotations, and/or symbolic annotations.

The graphs 1620 may indicate that the number of visits per day by a telepresence device may positively correspond to an outcome rating of a patient. A user may visualize the coordinate system 1610 and determine that a telepresence device should visit each patient more frequently. The viewing level 1600 includes only the number of visits per day and the number of stethoscope usages selected via telepresence device statistic selection panel 1640. The viewing level 1600 does not include any filtering via filter selection panel 1650.

Figure 17:
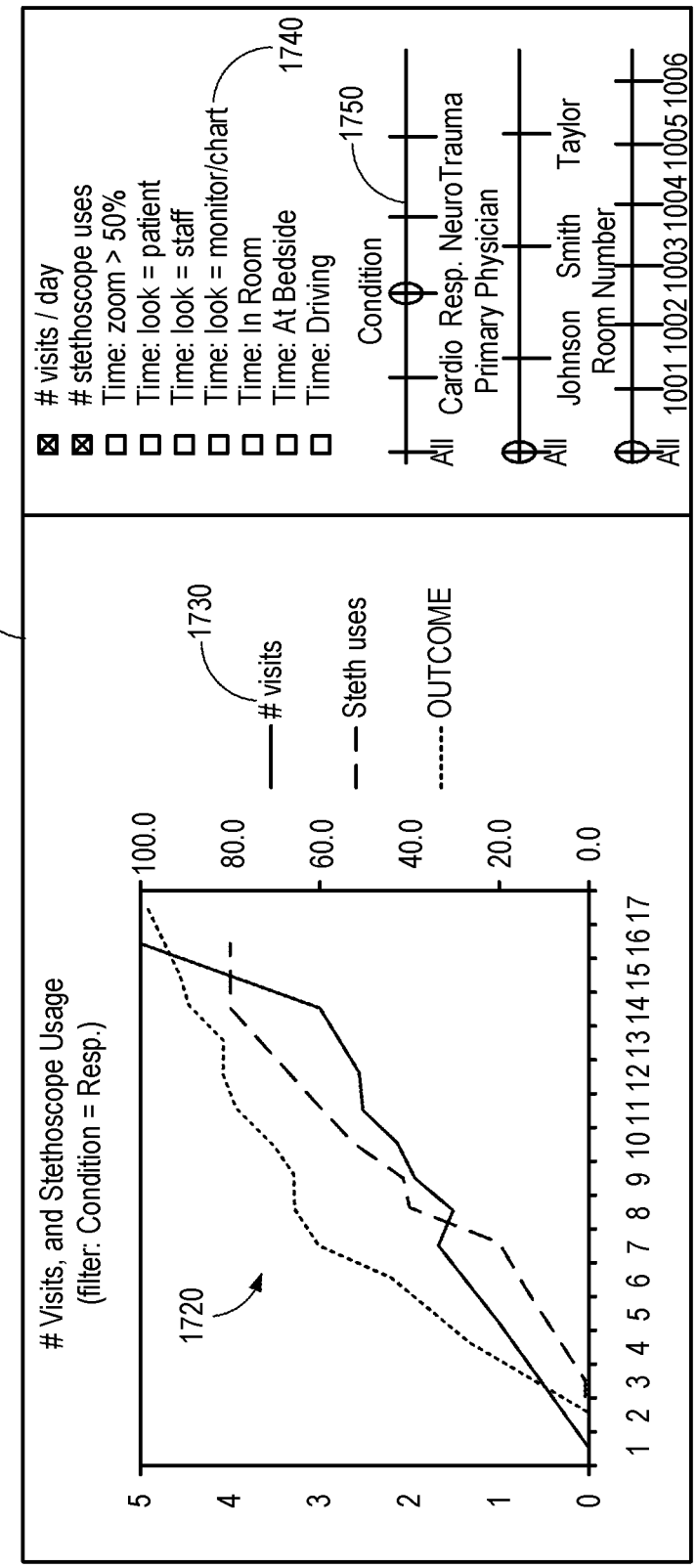
FIG. 17 illustrates a coordinate system including graphs of patient outcome ratings, a number of visits per day, and a number of stethoscope uses, where the patients included on the coordinate system are filtered based on a specific health condition.

FIG. 17 illustrates a viewing level 1700 including a coordinate system 1710 with graphs 1720 of patient outcome ratings, a number of visits per day, and a number of stethoscope uses, as can be seen in legend 1730. Accordingly, the graphs 1720 of FIG. 17 are the same as in FIG. 16; i.e., the selections made via telepresence device statistic selection panels 1740 and 1640 are the same. However, in FIG. 17, a condition filter is applied via filter selection panel 1750. The graphs 1720 of FIG. 17 are filtered to include only the data for patients whose primary condition is respiratory in nature.

Comparing FIGS. 16 and 17, it can be seen that the number of stethoscope uses in with patients whose primary condition is respiratory in nature correlates with the outcome ratings (FIG. 17), while the number of stethoscope uses in patients with all types of conditions (unfiltered) does not correlate with the outcome ratings (FIG. 16). Accordingly, it may be useful to adjust the condition, primary physician, and room number filters available in filter selection panel 1750 in order to facilitate the discovery of additional correlations within the data sets.

Figure 18A:
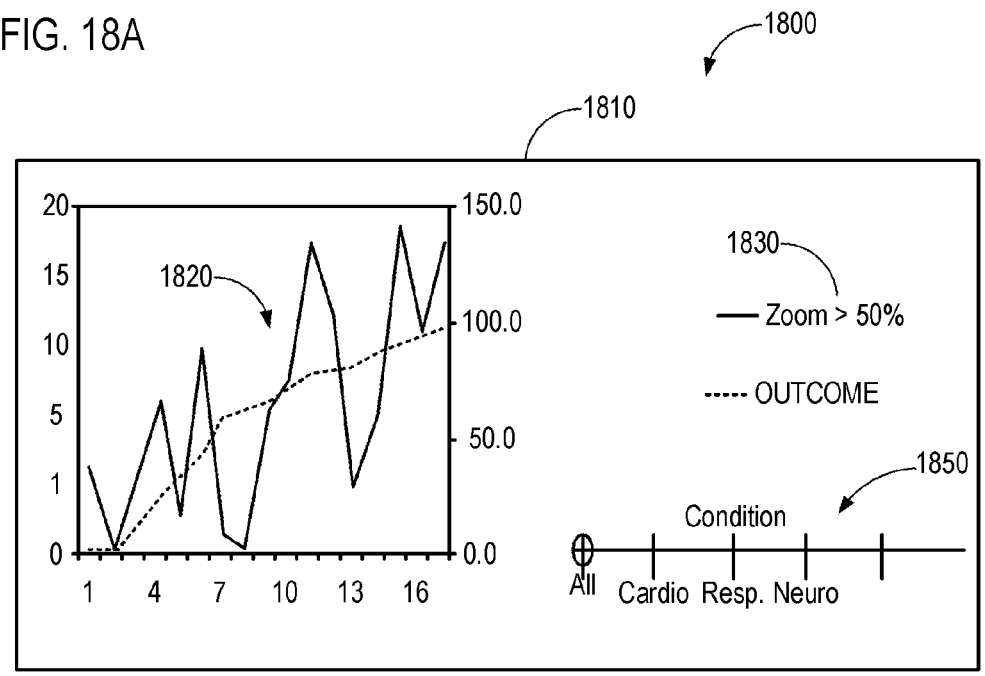
FIG. 18A illustrates a graph of patient outcome ratings and an amount of time a camera of a telepresence device is zoomed greater than 50%.

FIG. 18A illustrates a viewing level 1800 including a coordinate system 1810 with graphs 1820. Graphs 1820 include an outcome rating and the amount of time a camera of a telepresence device is zoomed greater than 50%, as illustrated in the legend 1830. The filters in filter selection panel 1850 are set to "all." As can be seen in FIG. 18A, there does not seem to be a correlation between the amount of time the camera of the telepresence device is zoomed greater than 50% and the outcome rating of the patient.

Figure 18B:
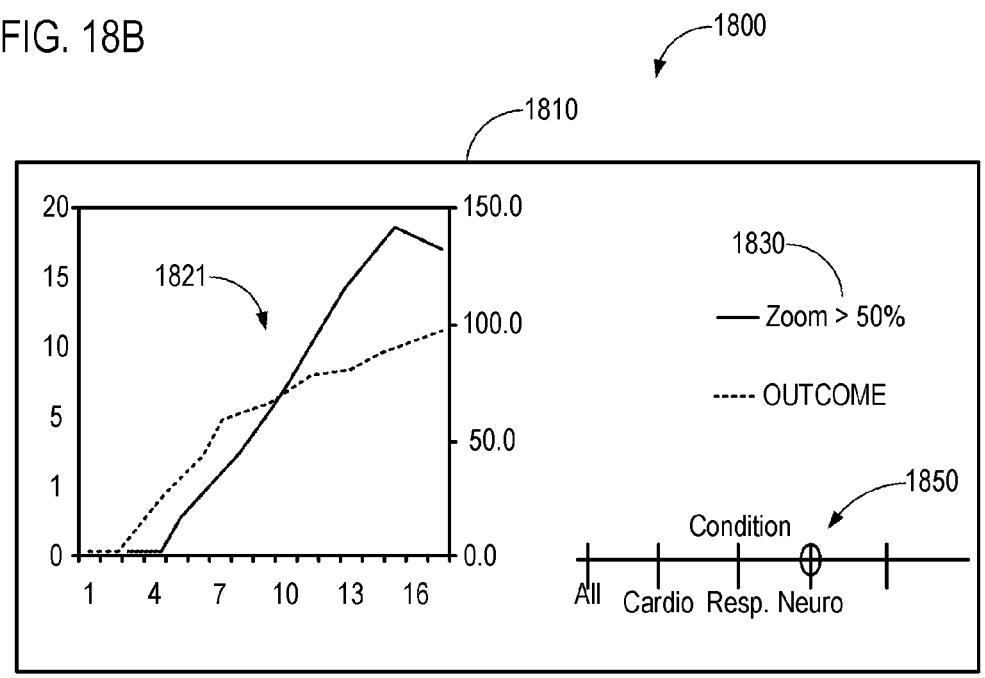
FIG. 18B illustrates a graph of patient outcome ratings and an amount of time a camera of a telepresence device is zoomed greater than 50%, where the patients included on the coordinate system are filtered to include only those with a neurological condition.

However, looking at FIG. 18B, it can be seen that by applying a condition filter within the filter selection panel 1850 to visualize only those patients whose primary condition is neurological in nature, a correlation between camera usage and outcome rating can be seen. Accordingly, graphs 1821 illustrate that for patients with neurological conditions, using the camera of a telepresence device zoomed to 50% or greater is correlated to the outcome rating of the patient.

Figure 19:
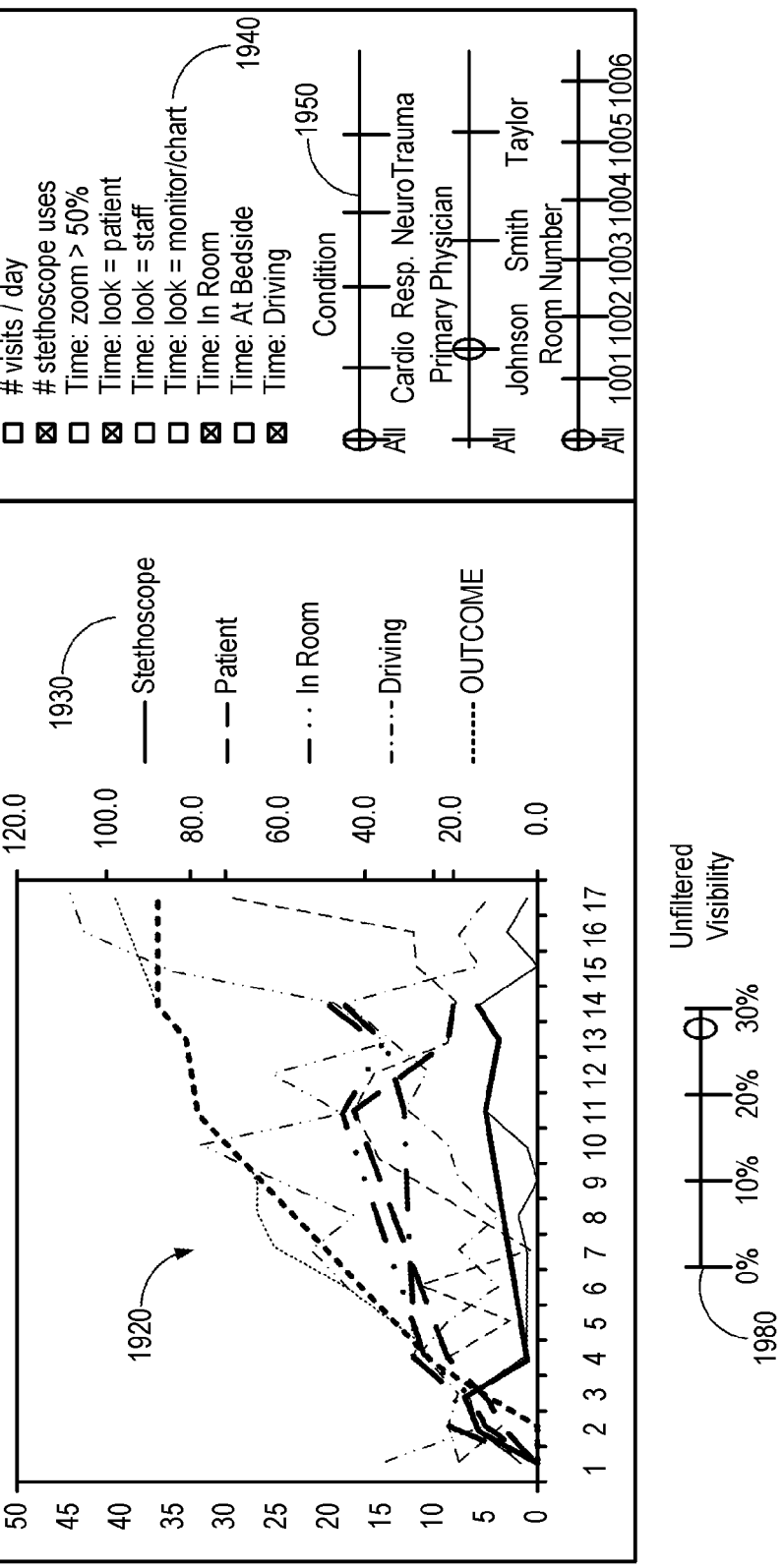
FIG. 19 illustrates a graph of patient outcome ratings and selected telepresence device statistics, including a selection of patients filtered by physician contrasted with similar telepresence device statistics for all of the patients (unfiltered).

FIG. 19 illustrates a viewing level 1900 with a coordinate system 1910 that includes numerous graphs 1920 selected via the telepresence device statistic selection panel 1940. Each of the graphs 1920 is described in the legend 1930. A physician filter may be applied via the filter selection panel 1950. Accordingly, data associated with a particular physician is graphed. An unfiltered visibility slider 1980 may allow the complete set of data to be partially visible. This may allow a user to visualize the data of a particular physician with respect to all other physicians. Accordingly, graphs 1920 include data associated with the selected physician in bold, and the complete set of data in a thinner line. The same line pattern (dashes) is used for each telepresence device statistic. In various embodiments, the unfiltered visibility slider 1980 may allow a user to select an opacity percentage between 0 and 100. The graphs 1920 may be distinguishable using various line colors, line shading gradients, line color gradients, line thicknesses, line patterns, line hues, numerical annotations, and/or symbolic annotations.

Figure 20:
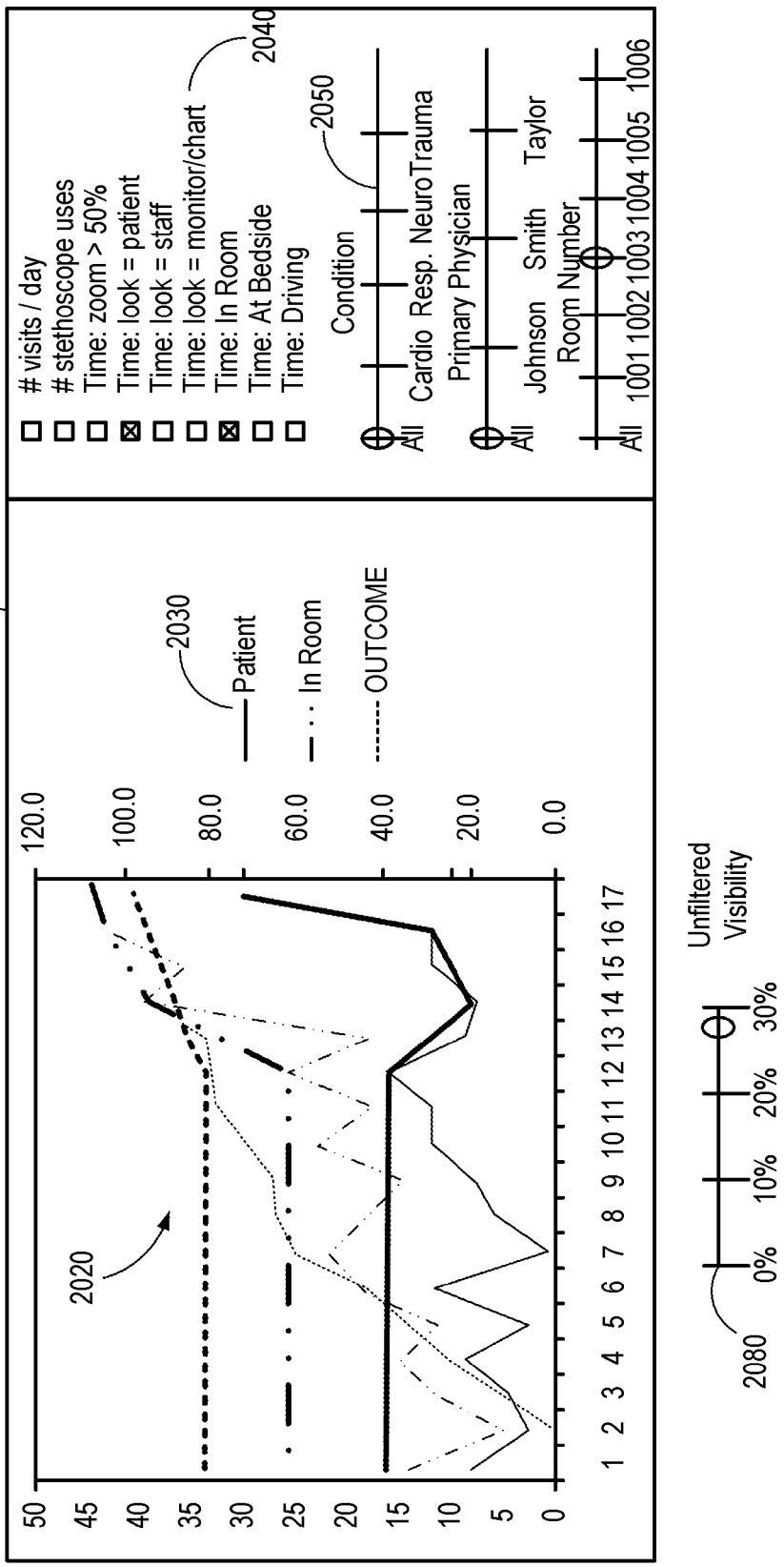
FIG. 20 illustrates a graph of patient outcome ratings and selected telepresence device statistics, including a selection of patients filtered by room number contrasted with similar telepresence device statistics for all of the patients (unfiltered).

FIG. 20 illustrates a viewing level 2000 with a coordinate system 2010 that includes numerous graphs 2020 selected via the telepresence device statistic selection panel 2040. Each of the graphs 2020 may be described in the legend 2030. A room number filter may be applied via the filter selection panel 2050. Accordingly, data associated with patients who stayed in a particular room is graphed in graphs 2020. An unfiltered visibility slider 2080 may allow data for the selected room to be compared with that of all of the rooms, with the data associated with all of the rooms shown as slightly translucent, with thinner lines, with different hues, and/or the like. Such a viewing level 2000 may allow a user to determine which rooms have the highest success rate. It may be that rooms closest to a docking station of a telepresence device have a higher rate of visits by the telepresence device and, accordingly, a higher outcome rating. The presently described visualization tool may allow a user to quickly and easily filter, organize, and selectively display numerous data points in order to determine correlations that may improve overall medical care in a healthcare facility.

Figure 21:
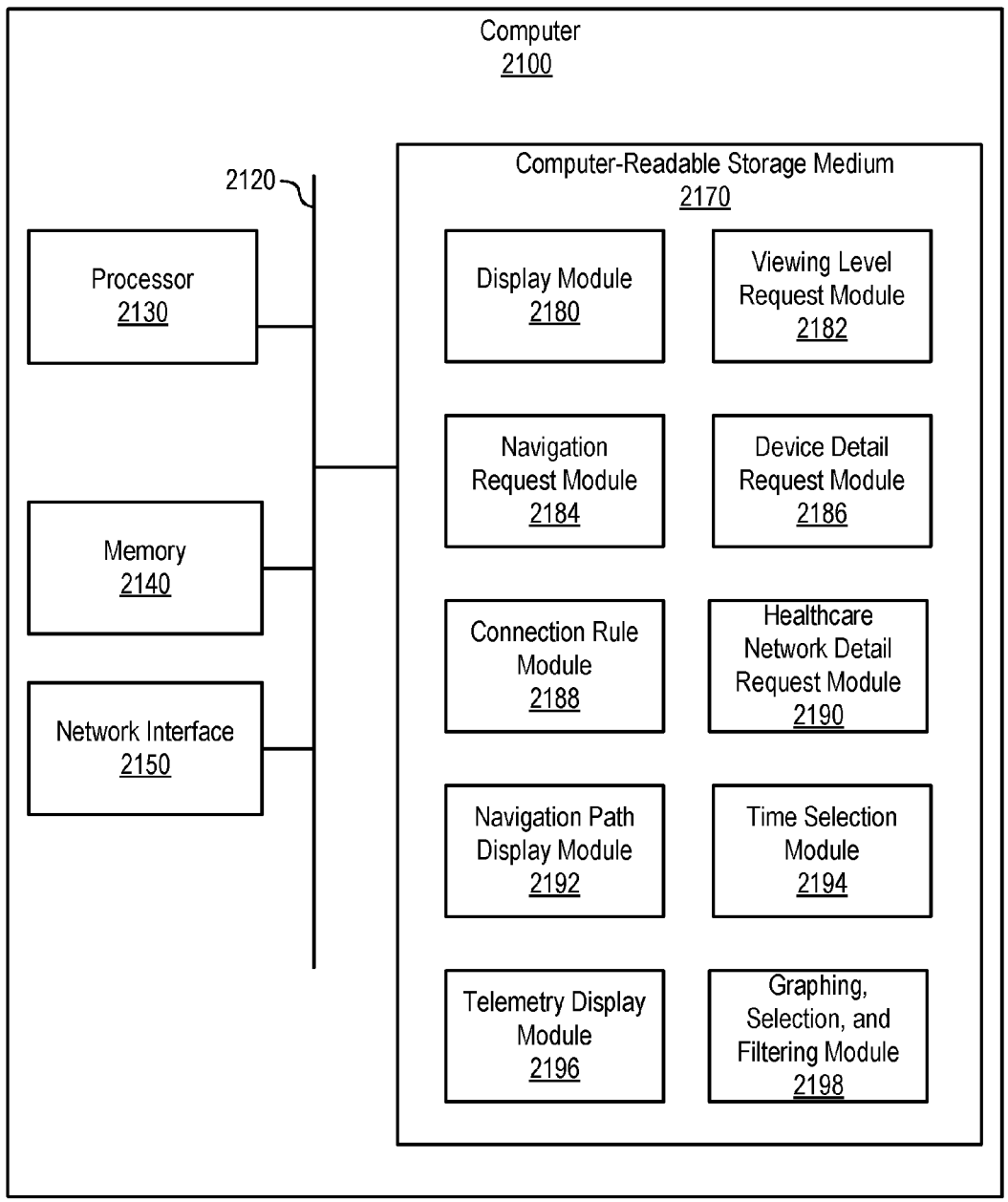
FIG. 21 illustrates a functional block diagram of a computer system including various modules for a telepresence network visualization and management system.

FIG. 21 illustrates a functional block diagram of a computer system 2100 including various modules 2170 for a telepresence network visualization and management system. As illustrated, computer system 2100 may include a processor 2130, memory (such as RAM) 2140, and a network interface 2150 connected via a bus 2120. The bus 2120 may also connect a computer-readable storage medium 2170. The computer-readable storage medium 2170 may include various modules, such as a display module 2180, a viewing level request module 2182, a navigation request module 2184, a device detail request module 2186, a connection rule module 2188, and a healthcare network detail request module 2190. Additional modules may be included, or some modules may be omitted, in order for a computer system to perform any of the server-side or client-side functions of the various systems and methods described herein.

The display module 2180 may be configured to display a viewing level of a telepresence network on a geographical representation. Display module 2180 may be configured to display any of the various viewing levels described herein, including the various selection panels, filtering panels, and graphical representations. The viewing level request module 2182 may be configured to receive a viewing request to cause the display module 2180 to provide a second viewing level. The navigation request module 2184 may be configured to receive a navigational request to navigate within the geographical representation.

The device detail request module 2186 may be configured to receive a detail request to cause the display module 2180 to display a third viewing level, the third viewing level including information associated with one or more telepresence devices. The connection rule module 2188 may be configured to allow for the management of a connection rule governing telepresence devices. The healthcare network detail request module 2190 may be configured to receive a healthcare network detail request to cause the display module 2180 to display a fourth viewing level, the fourth viewing level including information associated with healthcare facilities.

A navigation path display module 2192 may be configured to display navigational paths traversed by a telepresence device on a plan map. The navigational paths may be displayed in such a way that they are distinguishable based on drive mode, as described herein. A time selection module 2194 may be configured to allow a user to specify a time or time period. The time selection module 2194 may receive user input via a calendar, a clock, a slider, numerical inputs, and/or the like. A telemetry display module 2196 may be configured to display historical and/or current telemetry data for a selected time or time period for a selected room on a plan map.

A graphing, selection, and filtering module 2198 may be configured to provide graphical views and receive selection inputs and filtering inputs as described in conjunction with FIGS. 14-20. The graphs produced by graphing, selection, and filtering module 2198 may be locally rendered or remotely rendered, and may be stored in memory 2140 or rendered in real-time by processor 2130 or another processor (such as a specialized processor). Any of the described viewing levels, communications systems, inputs, and modules may be implemented in any combination of hardware, firmware, and software. Moreover, one or more functions may be performed remotely or stored remotely as is found useful.

Many changes may be made to the details of the above-described embodiments without departing from the underlying principles and scope of the present disclosure. Accordingly, the scope of the presently described systems and methods should be determined only by the following claims.

What is claimed:

1. A computer program product, comprising a non-transitory computer-readable medium having executable computer program code, the computer program code configured to cause a computer to:
   receive a plurality of telepresence device statistics, each telepresence device statistic comprising information associated with an action performed via a telepresence device with respect to each of a plurality of patients;
   display a telepresence device statistic selection panel configured to allow a user to select one or more of the plurality of telepresence device statistics;
   receive a selection of at least one telepresence device statistic via the telepresence device statistic selection panel; and
   display a visual representation of the selected at least one telepresence device statistic, wherein the computer program code is further configured to cause the computer to:
   receive a rating for each of the plurality of patients treated via a telepresence device, the ratings associated with a health aspect of each of the plurality of patients; and
   wherein to display the visual representation the computer program code is further configured to cause the computer to:
   display a graph of the at least one selected telepresence device statistic with respect to each of the plurality of patients on a coordinate system; and
   display an indication of the rating for each of the plurality of patients with respect to each of the plurality of patients displayed on the coordinate system.

2. The computer program product of claim 1, wherein the rating for each of the plurality of patients comprises an outcome rating corresponding to a health aspect of a discharged patient.

3. A computer program product, comprising a non-transitory computer-readable medium having executable computer program code, the computer program code configured to cause a computer to:
   receive a plurality of telepresence device statistics, each telepresence device statistic comprising information associated with an action performed via a telepresence device with respect to each of a plurality of patients;
   display a telepresence device statistic selection panel configured to allow a user to select one or more of the plurality of telepresence device statistics;
   receive a selection of at least one telepresence device statistic via the telepresence device statistic selection panel; and
   display a visual representation of the selected at least one telepresence device statistic, wherein the computer program code is further configured to cause a computer to:
   receive a primary patient condition for each of the plurality of patients;
   display a filter selection panel comprising a condition filter input, the condition filter input configured to allow a user to select one or more primary patient conditions;
   receive at least one selection via the filter selection panel;
   remove from the visual representation any telepresence device statistic not associated with the selections made via the filter selection panel; and
   update the visual representation of the at least one selected telepresence device statistic based on the selections made via the filter selection panel.

4. A computer program product, comprising a non-transitory computer-readable medium having executable computer program code, the computer program code configured to cause a computer to:
- receive a plurality of telepresence device statistics, each telepresence device statistic comprising information associated with an action performed via a telepresence device with respect to each of a plurality of patients;
- display a telepresence device statistic selection panel configured to allow a user to select one or more of the plurality of telepresence device statistics;
- receive a selection of at least one telepresence device statistic via the telepresence device statistic selection panel; and
- display a visual representation of the selected at least one telepresence device statistic, wherein the computer program code is further configured to cause a computer to:
- receive information identifying a primary physician for each of the plurality of patients;
- display a filter selection panel comprising a primary physician filter input, the primary physician filter input configured to allow a user to select one or more primary physicians;
- receive at least one selection via the filter selection panel;
- remove from the visual representation any of the telepresence device statistics not associated with the at least one selection made via the filter selection panel; and
- update the visual representation of the at least one selected telepresence device statistic based on the selections made via the filter selection panel.

5. A computer program product, comprising a non-transitory computer-readable medium having executable computer program code, the computer program code configured to cause a computer to:
- receive a plurality of telepresence device statistics, each telepresence device statistic comprising information associated with an action performed via a telepresence device with respect to each of a plurality of patients;
- display a telepresence device statistic selection panel configured to allow a user to select one or more of the plurality of telepresence device statistics;
- receive a selection of at least one telepresence device statistic via the telepresence device statistic selection panel; and
- display a visual representation of the selected at least one telepresence device statistic, wherein the computer program code is further configured to cause a computer to:
- receive information identifying a room associated with each of the plurality of patients;
- display a filter selection panel comprising a room filter input, the room filter input configured to allow a user to select one or more rooms of a healthcare facility;
- receive at least one selection via the filter selection panel;
- remove from the visual representation any of the plurality of patients not associated with the at least one selection made via the filter selection panel; and
- update the visual representation of the at least one selected telepresence device statistic based on the selections made via the filter selection panel.

6. A computer program product, comprising a non-transitory computer-readable medium having executable computer program code, the computer program code configured to cause a computer to:
- receive a plurality of telepresence device statistics, each telepresence device statistic comprising information associated with an action performed via a telepresence device with respect to each of a plurality of patients;
- display a telepresence device statistic selection panel configured to allow a user to select one or more of the plurality of telepresence device statistics;
- receive a selection of at least one telepresence device statistic via the telepresence device statistic selection panel; and
- display a visual representation of the selected at least one telepresence device statistic, wherein the plurality of telepresence device statistics comprises a telepresence device statistic indicating how many visits were made to each of the plurality of patients by the telepresence device during a time period.

7. A computer program product, comprising a non-transitory computer-readable medium having executable computer program code, the computer program code configured to cause a computer to:
- receive a plurality of telepresence device statistics, each telepresence device statistic comprising information associated with an action performed via a telepresence device with respect to each of a plurality of patients;
- display a telepresence device statistic selection panel configured to allow a user to select one or more of the plurality of telepresence device statistics;
- receive a selection of at least one telepresence device statistic via the telepresence device statistic selection panel; and
- display a visual representation of the selected at least one telepresence device statistic, wherein the plurality of telepresence device statistics comprises a telepresence device statistic associated with a usage of a telepresence device accessory on each of the plurality of patients during a time period, the telepresence device statistic configured to measure a physiological parameter.

8. The computer program product of claim 7, wherein the telepresence device accessory is configured to determine one of a blood pressure, a heart rate, a temperature, a respiration rate, and electrocardiogram information.

9. The computer program product of claim 7, wherein the telepresence device accessory comprises one of a stethoscope, an otoscope, and a medical imaging device.

10. A computer program product, comprising a non-transitory computer-readable medium having executable computer program code, the computer program code configured to cause a computer to:
- receive a plurality of telepresence device statistics, each telepresence device statistic comprising information associated with an action performed via a telepresence device with respect to each of a plurality of patients;
- display a telepresence device statistic selection panel configured to allow a user to select one or more of the plurality of telepresence device statistics;
- receive a selection of at least one telepresence device statistic via the telepresence device statistic selection panel; and
- display a visual representation of the selected at least one telepresence device statistic, wherein the plurality of telepresence device statistics comprises a telepresence device statistic associated with a usage of a camera of the telepresence device during a time period.

11. A computer program product, comprising a non-transitory computer-readable medium having executable computer program code, the computer program code configured to cause a computer to:
- receive a plurality of telepresence device statistics, each telepresence device statistic comprising information associated with an action performed via a telepresence device with respect to each of a plurality of patients;

display a telepresence device statistic selection panel configured to allow a user to select one or more of the plurality of telepresence device statistics;

receive a selection of at least one telepresence device statistic via the telepresence device statistic selection panel; and display a visual representation of the selected at least one telepresence device statistic, wherein the plurality of telepresence device statistics comprises a telepresence device statistic associated with a location of the telepresence device relative to each of the plurality of patients during a time period.

* * * * *